United States Patent
Kim

(10) Patent No.: US 7,590,510 B2
(45) Date of Patent: Sep. 15, 2009

(54) SYSTEMS AND METHODS FOR IDENTIFYING DAMAGE IN A STRUCTURE

(75) Inventor: Hyeung-Yun Kim, Palo Alto, CA (US)

(73) Assignee: Advanced Structure Monitoring, Inc., Cupertino, CA (US)

(*) Notice: Subject to any disclaimer, the term of this patent is extended or adjusted under 35 U.S.C. 154(b) by 4 days.

(21) Appl. No.: 11/827,350

(22) Filed: Jul. 10, 2007

(65) Prior Publication Data

US 2007/0260427 A1    Nov. 8, 2007

Related U.S. Application Data

(62) Division of application No. 10/942,714, filed on Sep. 16, 2004, now Pat. No. 7,286,964.

(60) Provisional application No. 60/505,120, filed on Sep. 22, 2003.

(51) Int. Cl.
*G06F 11/30* (2006.01)

(52) U.S. Cl. .................. 702/183; 340/870.15

(58) Field of Classification Search ............ 702/33–40, 702/81, 182–183, 185, 188; 703/1, 6–7; 714/25–26, 47–48; 340/870.11, 870.15, 340/3.1, 3.3, 3.31–3.32
See application file for complete search history.

(56) References Cited

U.S. PATENT DOCUMENTS

| | | |
|---|---|---|
| 2,177,629 A | 10/1939 | Foster |
| 3,427,481 A | 2/1969 | Lenahan et al. |
| 3,593,048 A | 7/1971 | Dunegan et al. |
| 3,672,210 A | 6/1972 | Cressman et al. |
| 4,011,472 A | 3/1977 | Feng |
| 4,012,952 A | 3/1977 | Dory |
| 4,480,480 A | 11/1984 | Scott et al. |
| 4,534,222 A | 8/1985 | Finch et al. |
| 4,665,750 A | 5/1987 | Rogers |
| 4,961,176 A | 10/1990 | Tanaka et al. |
| 5,184,516 A | 2/1993 | Blazic et al. |
| 5,195,046 A | 3/1993 | Gerardi et al. |
| 5,440,300 A | 8/1995 | Spillman, Jr. |
| 5,452,264 A | 9/1995 | Holroyd |
| 5,524,491 A | 6/1996 | Cavalloni |

(Continued)

OTHER PUBLICATIONS

Kim, H.Y. and Hwang, W. *"Estimation Of Normal Mode And Other System Parameters Of Composite Laminated Plates"*, Composite Structures, 2001.

(Continued)

*Primary Examiner*—Eliseo Ramos Feliciano
*Assistant Examiner*—Mary C Baran
(74) *Attorney, Agent, or Firm*—Patent Office of Dr. Chung Sik Park

(57) ABSTRACT

Systems, methods and recordable media for identifying damage in a structure. A method includes the steps of: obtaining a plurality of damage index values for a network coupled to the structure, wherein each of the damage index values is a quantity to be affected by damage in the structure; generating a distribution of damage index value over a surface using the obtained damage index values; and identifying the damage by analyzing the distribution.

30 Claims, 29 Drawing Sheets
(1 of 29 Drawing Sheet(s) Filed in Color)

U.S. PATENT DOCUMENTS

| | | | |
|---|---|---|---|
| 5,524,625 A | 6/1996 | Okazaki et al. | |
| 5,625,150 A | 4/1997 | Greene et al. | |
| 5,663,504 A | 9/1997 | Kluft | |
| 5,677,488 A | 10/1997 | Monahan et al. | |
| 5,710,723 A | 1/1998 | Hoth et al. | |
| 5,814,729 A | 9/1998 | Wu et al. | |
| 5,854,994 A | 12/1998 | Canada et al. | |
| 6,115,653 A | 9/2000 | Bergstrom et al. | |
| 6,118,850 A * | 9/2000 | Mayo et al. | 378/83 |
| 6,161,434 A | 12/2000 | Fink et al. | |
| 6,166,653 A | 12/2000 | Schulmeyer et al. | |
| 6,170,334 B1 * | 1/2001 | Paulson | 73/587 |
| 6,182,512 B1 | 2/2001 | Lorraine | |
| 6,204,920 B1 | 3/2001 | Ellerbrock et al. | |
| 6,208,949 B1 * | 3/2001 | Eatwell | 702/189 |
| 6,370,964 B1 | 4/2002 | Chang et al. | |
| 6,396,262 B2 | 5/2002 | Light et al. | |
| 6,399,939 B1 | 6/2002 | Sundaresan et al. | |
| 6,496,782 B1 * | 12/2002 | Claus et al. | 702/40 |
| 6,628,567 B1 | 9/2003 | Prosser et al. | |
| 6,648,082 B2 * | 11/2003 | Schultz et al. | 175/39 |
| 6,655,922 B1 * | 12/2003 | Flek | 417/44.1 |
| 6,907,416 B2 * | 6/2005 | Tasooji et al. | 706/50 |
| 6,917,839 B2 * | 7/2005 | Bickford | 700/30 |
| 7,069,158 B2 * | 6/2006 | Gidwani | 702/56 |
| 7,117,742 B2 | 10/2006 | Kim | |
| 2002/0012478 A1 | 1/2002 | Thirion et al. | |
| 2002/0043560 A1 * | 4/2002 | Woods et al. | 235/438 |
| 2004/0206187 A1 | 10/2004 | Williams | |
| 2005/0002276 A1 | 1/2005 | Yogeswaren | |
| 2005/0195808 A1 | 9/2005 | Chen et al. | |
| 2006/0002368 A1 | 1/2006 | Budampati et al. | |
| 2006/0107084 A1 | 5/2006 | Taylor et al. | |

OTHER PUBLICATIONS

Kim, H.Y., "*Structural Dynamic System Reconstruction Method for Vibrating Structures*", Transaction of ASME, 2003.

Kim, H.Y., "*Vibration-Based Damage Identification Using Reconstructed FRFS In Composite Structures*", Journal of Sound and Vibration, 2003.

Kim, H.Y. and Hwang, W., " *Effect of Debonding On Natural Frequencies And Frequency Response Functions Of Honeycomb Sandwich Beams*", Composite Structures, 2001.

Moon, T.C., Kim, H.Y. and Hwang W., "*Natural-Frequency Reduction Model For Matrix-Dominated Fatigue Damage in Composite Laminates*", Composite Structures, 2003.

* cited by examiner

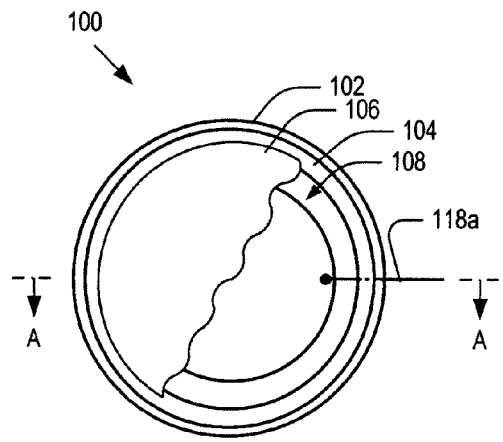
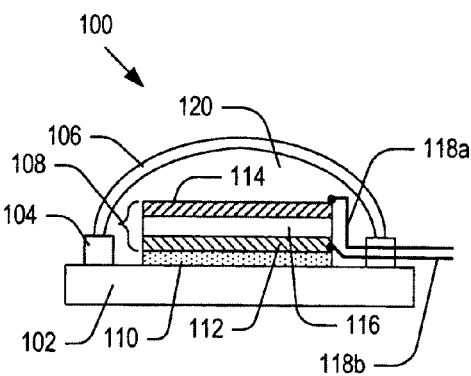
FIG. 1A            FIG. 1B
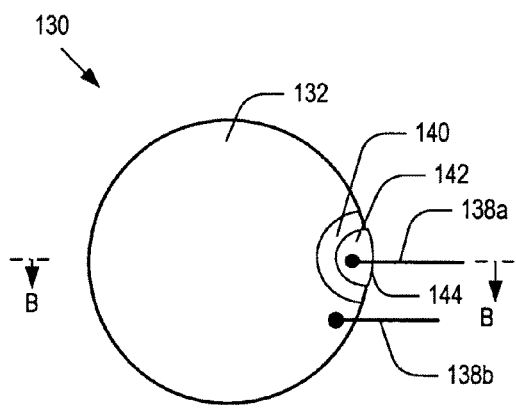
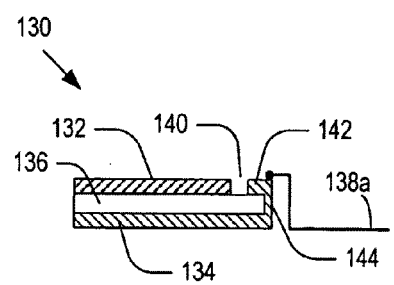
FIG. 1C (PRIOR ART)     FIG. 1D (PRIOR ART)

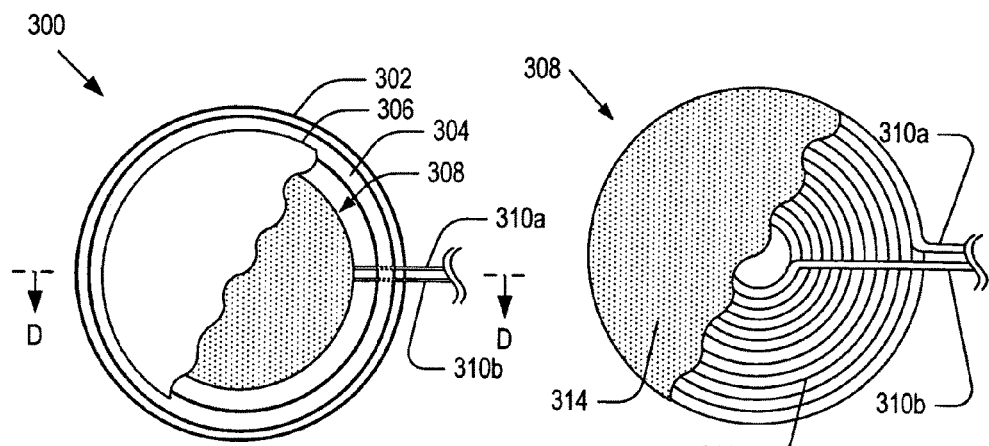
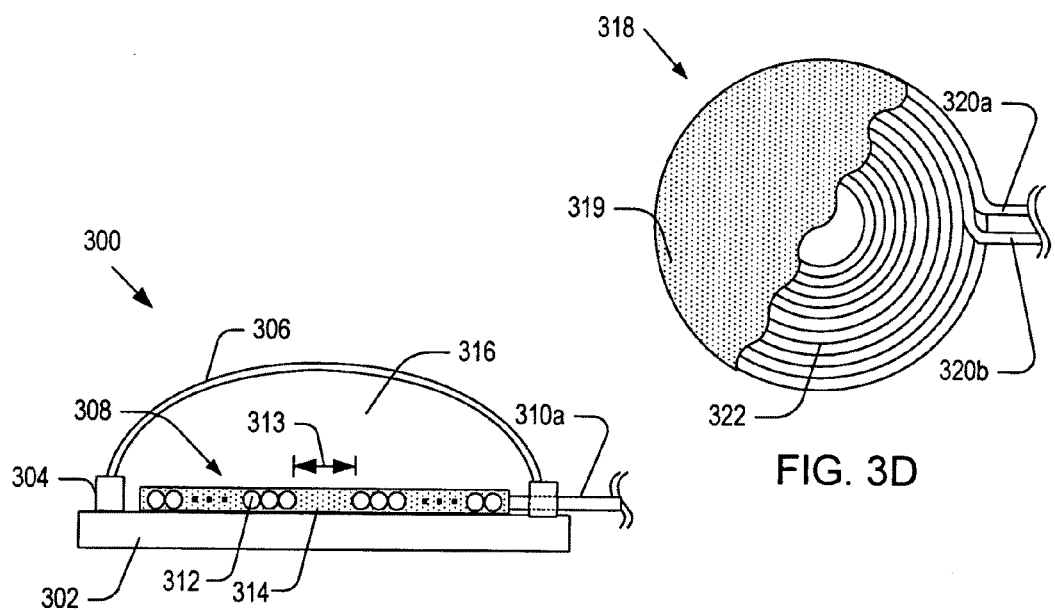
FIG. 3A
FIG. 3C
FIG. 3B
FIG. 3D

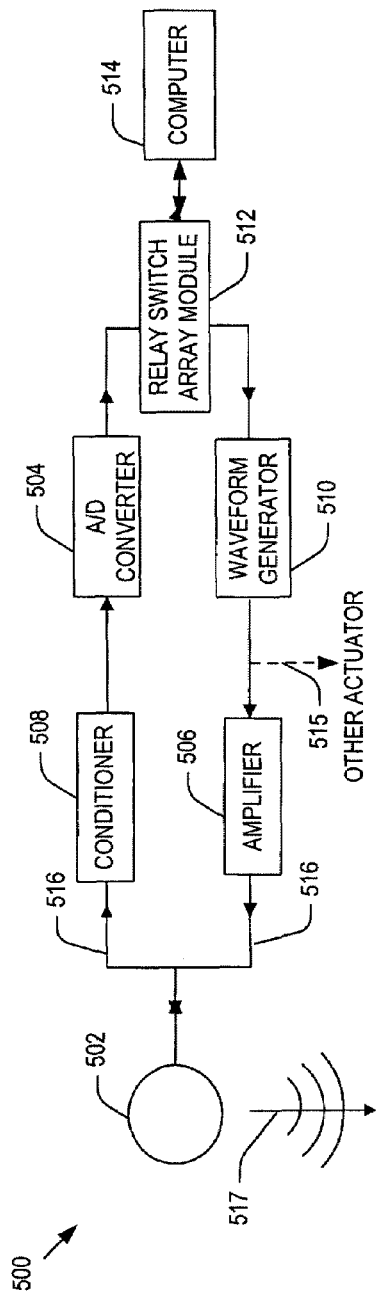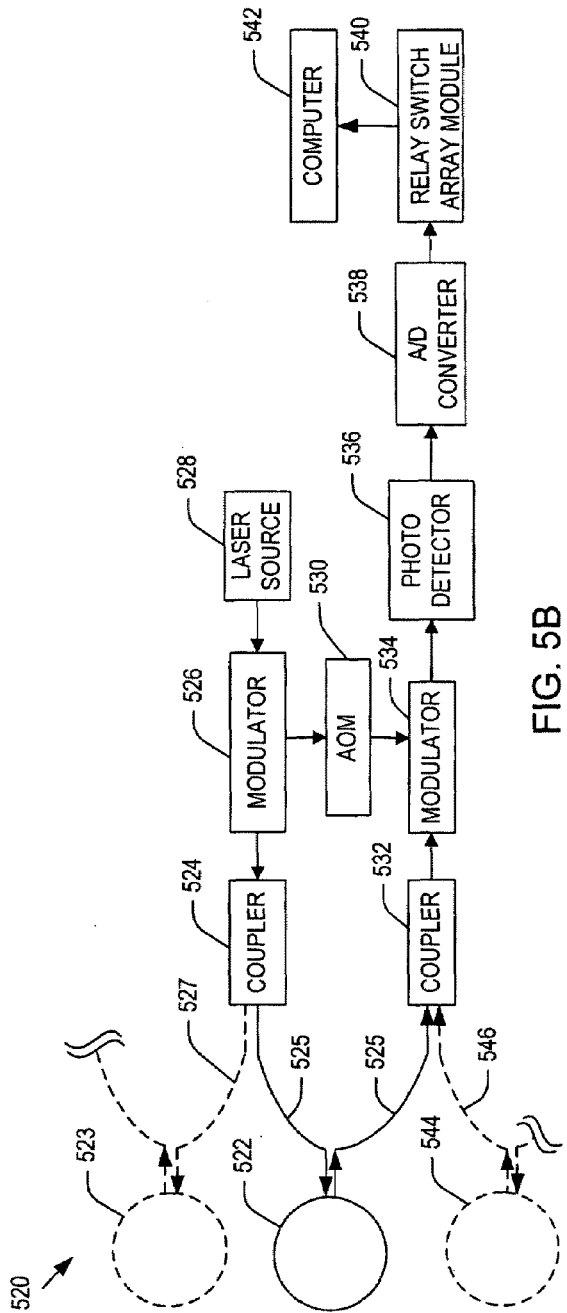

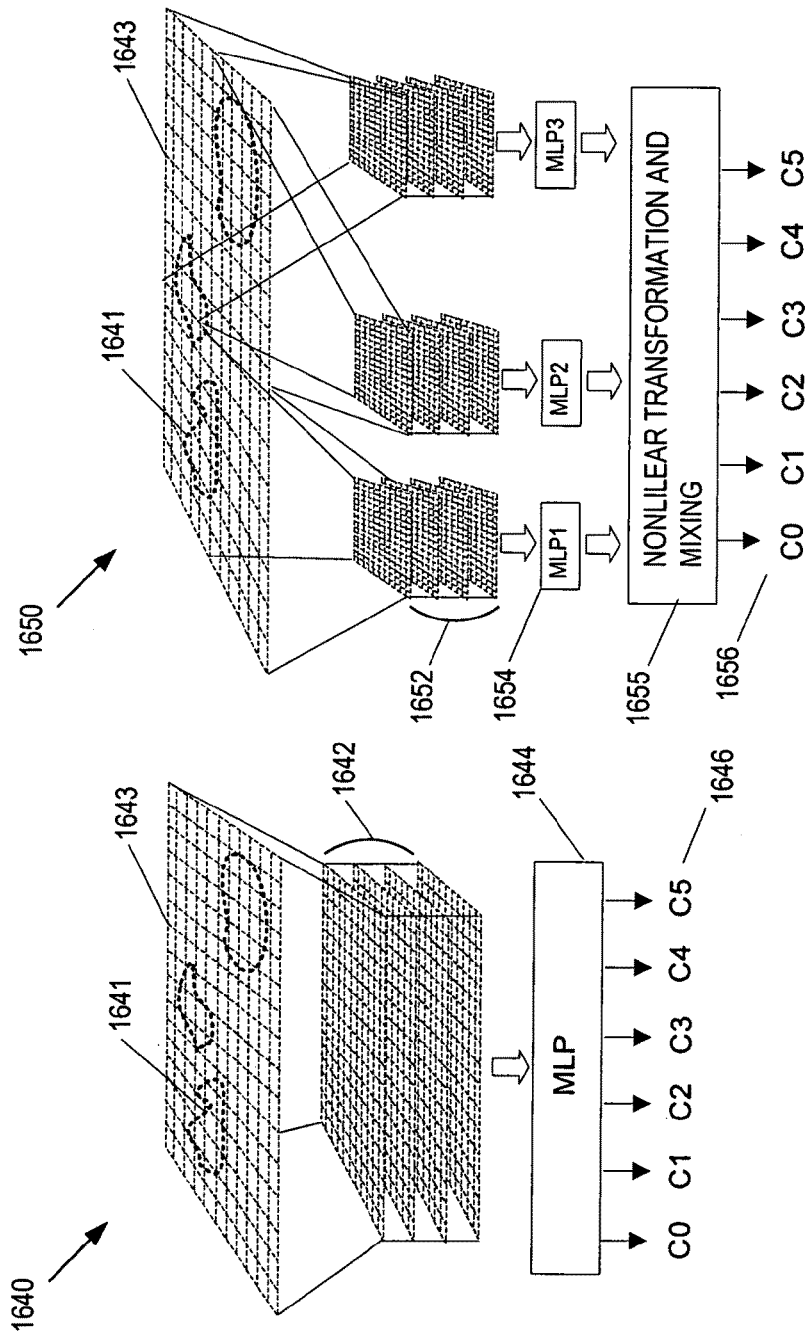

SYSTEMS AND METHODS FOR IDENTIFYING DAMAGE IN A STRUCTURE

CROSS REFERENCE TO RELATED APPLICATIONS

This application is a divisional application of application Ser. No. 10/942,714, entitled "Method for monitoring structural health conditions" by Kim, filed on Sep. 16, 2004, which claims the benefit of U.S. Provisional Applications No. 60/505,120, entitled "sensor and system for structural health monitoring," filed on Sep. 22, 2003, which is hereby incorporated herein by reference in its entirety.

FIELD OF INVENTION

The present invention relates to diagnostics of structures, and more particularly to methods for monitoring structural health conditions.

BACKGROUND OF THE INVENTION

As all structures in service require appropriate inspection and maintenance, they should be monitored for their integrity and health condition to prolong their life or to prevent catastrophic failure. Apparently, the structural health monitoring has become an important topic in recent years. Numerous methods have been employed to identify fault or damage of structures, where these methods may include conventional visual inspection and non-destructive techniques, such as ultrasonic and eddy current scanning, acoustic emission and X-ray inspection. These conventional methods require at least temporary removal of structures from service for inspection. Although still used for inspection of isolated locations, they are time-consuming and expensive.

With the advance of sensor technologies, new diagnostic techniques for in-situ structural integrity monitoring have been in significant progress. Typically, these new techniques utilize sensory systems of appropriate sensors and actuators built in host structures. However, these approaches have drawbacks and may not provide effective on-line methods to implement a reliable sensory network system and/or accurate monitoring methods that can diagnose, classify and forecast structural condition with the minimum intervention of human operators. For example, U.S. Pat. No. 5,814,729, issued to Wu et al., discloses a method that detects the changes of damping characteristics of vibrational waves in a laminated composite structure to locate delaminated regions in the structure. Piezoceramic devices are applied as actuators to generate the vibrational waves and fiber optic cables with different grating locations are used as sensors to catch the wave signals. A drawback of this system is that it cannot accommodate a large number of actuator arrays and, as a consequence, each of actuators and sensors must be placed individually. Since the damage detection is based on the changes of vibrational waves traveling along the line-of-sight paths between the actuators and sensors, this method fails to detect the damage located out of the paths and/or around the boundary of the structure.

Another approach for damage detection can be found in U.S. Pat. No. 5,184,516, issued to Blazic et al., that discloses a self-contained conformal circuit for structural health monitoring and assessment. This conformal circuit consists of a series of stacked layers and traces of strain sensors, where each sensor measures strain changes at its corresponding location to identify the defect of a conformal structure. The conformal circuit is a passive system, i.e., it does not have any actuator for generating signals. A similar passive sensory network system can be found in U.S. Pat. No. 6,399,939, issued to Mannur, J. et al. In Mannur '939 patent, a piezoceramic-fiber sensory system is disclosed having planner fibers embedded in a composite structure. A drawback of these passive methods is that they cannot monitor internal delamination and damages between the sensors. Moreover, these methods can detect the conditions of their host structures only in the local areas where the self-contained circuit and the piezoceramic-fiber are affixed.

One method for detecting damages in a structure is taught by U.S. Pat. No. 6,370,964 (Chang et al.). Chang et al. discloses a sensory network layer, called Stanford Multi-Actuator-Receiver Transduction (SMART) Layer. The SMART Layer® includes piezoceramic sensors/actuators equidistantly placed and cured with flexible dielectric films sandwiching the piezoceramic sensors/actuators (or, shortly, piezoceramics). The actuators generate acoustic waves and sensors receive/transform the acoustic waves into electric signals. To connect the piezoceramics to an electronic box, metallic clad wires are etched using the conventional flexible circuitry technique and laminated between the substrates. As a consequence, a considerable amount of the flexible substrate area is needed to cover the clad wire regions. In addition, the SMART Layer® needs to be cured with its host structure made of laminated composite layers. Due to the internal stress caused by a high temperature cycle during the curing process, the piezoceramics in the SMART Layer® can be micro-fractured. Also, the substrate of the SMART Layer® can be easily separated from the host structure. Moreover, it is very difficult to insert or attach the SMART Layer® to its host structure having a curved section and, as a consequence, a compressive load applied to the curved section can easily fold the clad wires. Fractured piezoceramics and the folded wires may be susceptible to electromagnetic interference noise and provide misleading electrical signals. In harsh environments, such as thermal stress, field shock and vibration, the SMART Layer® may not be a robust and unreliable tool for monitoring structural health. Furthermore, the replacement of damaged and/or defective actuators/sensors may be costly as the host structure needs to be dismantled.

Another method for detecting damages in a structure is taught by U.S. Pat. No. 6,396,262 (Light et al.). Light et al. discloses a magnetostrictive sensor for inspecting structural damages, where the sensor includes a ferromagnetic strip and a coil closely located to the strip. The major drawback of this system is that the system cannot be designed to accommodate an array of sensors and, consequently, cannot detect internal damages located between sensors.

Due to the mentioned drawbacks, the methodologies for analyzing data that are implemented in these conventional systems may have limitations in monitoring the host structures in an accurate and efficient manner. Thus, there is a need for new and efficient methodologies for analyzing and interpreting the data from the host systems to determine structural conditions and to prognosticate failures.

OBJECTS AND ADVANTAGES

Accordingly, it is one object of the invention to provide an accurate technique for determining the structural condition by using different types of methods, such as bisection, intersection, and adaptive-neural-fuzzy-inference positioning of network paths, where the technique is incorporated with convex-set interpolation.

It is another object of the invention to provide a reliable technique for determining the structural condition by integrating the computed tomography algorithms for different structural condition indices.

It is yet another object of the invention to provide a method for interpreting the structural condition by the use of a hyperspectral tomography cube and a structural condition manifold.

It is still another object of the invention to provide a technique for classifying the structural condition by the use of a codebook-template based classifier, where the technique is incorporated with the multilayer perception on the tomography of a structure.

It is a further object of the invention to provide a prognostic technique for forecasting structural condition by modeling the diagnostic network system and updating its parameters, where the technique is incorporated with system identification and a supervised learning algorithm.

SUMMARY OF THE INVENTION

These and other objects and advantages are attained by a structural health monitoring software that comprises interrogation, processing, classification and prognosis modules and analyses data from a diagnostic network patch (DNP) system that is attached to a host composite and/or metallic structure. The DNP system contains actuators/sensors and provides an internal wave-ray communication network in the host structure by transmitting acoustic wave impulses (or, equivalently, Lamb waves) between the actuators/sensors.

According to one aspect of the present invention, a method of identifying damage in a structure, includes the steps of: obtaining a plurality of damage index values for a network coupled to a structure, each of the damage index values being a quantity to be affected by damage in the structure; generating, by use of a computer process, a distribution of damage index value over a surface using the obtained damage index values; and identifying the damage by analyzing the distribution.

According to another aspect of the present invention, a computer readable medium carries one or more sequences of instructions for identifying damage in a structure, wherein execution of one or more sequences of instructions by one or more processors causes the one or more processors to perform the steps of: obtaining a plurality of damage index values for a network coupled to a structure, each of the damage index values being a quantity to be affected by damage in the structure; generating, by use of a computer process, a distribution of damage index value over a surface using the obtained damage index values; and identifying the damage by analyzing the distribution.

According to still another aspect of the present invention, a system for identifying damage in a structure includes: means for obtaining a plurality of damage index values for a network coupled to the structure, each of the damage index values being a quantity to be affected by damage in the structure; means for generating, by use of a computer process, a distribution of damage index value over a surface using the obtained damage index values; and means for identifying the damage by analyzing the distribution.

These and other advantages and features of the invention will become apparent to those persons skilled in the art upon reading the details of the invention as more fully described below.

BRIEF DESCRIPTION OF THE DRAWINGS

The application file contains at least one drawing executed in color. Copies of this patent application publication with color drawings will be provided by the U.S. Patent and Trademark Office upon request and payment of the necessary fee.

FIG. 1A is a schematic top cut-away view of a patch sensor in accordance with one embodiment of the present invention.

FIG. 1B is a schematic side cross-sectional view of the patch sensor shown in FIG. 1A.

FIG. 1C is a schematic top view of a typical piezoelectric device that may be used in the patch sensor of FIG. 1A.

FIG. 1D is a schematic side cross-sectional view of the typical piezoelectric device in FIG. 1C.

FIG. 3A is a schematic top cut-away view of an optical fiber patch sensor in accordance with one embodiment of the present invention.

FIG. 3B is a schematic side cross-sectional view of the optical fiber patch sensor shown in FIG. 3A.

FIG. 3C is a schematic top cut-away view of the optical fiber coil contained in the optical fiber patch sensor of FIG. 3A.

FIG. 3D is a schematic top cut-away view of an alternative embodiment of the optical fiber coil shown in FIG. 3C.

FIG. 5A is a schematic diagram of an interrogation system including a sensor/actuator device in accordance with one embodiment of the present invention.

FIG. 5B is a schematic diagram of an interrogation system including a sensor in accordance with one embodiment of the present invention.

FIG. 16C is a schematic diagram illustrating a fully-connected network classifier for classifying a structural condition in accordance with one embodiment of the present invention.

FIG. 16D is a schematic diagram illustrating modular network classifiers for classifying structural conditions in accordance with one embodiment of the present invention.

DETAILED DESCRIPTION OF THE PREFERRED EMBODIMENTS

Figures 1E, 1F:
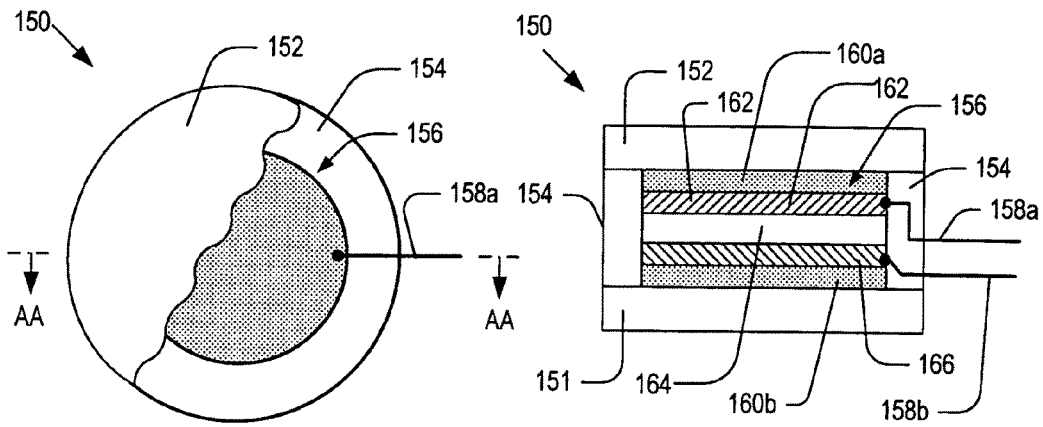
FIG. 1E is a schematic top cut-away view of a patch sensor in accordance with another embodiment of the present invention.
FIG. 1F is a schematic side cross-sectional view of the patch sensor shown in FIG. 1E.

Although the following detained description contains many specifics for the purposes of illustration, those of ordinary skill in the art will appreciate that many variations and alterations to the following detains are within the scope of the invention. Accordingly, the following embodiments of the invention are set forth without any loss of generality to, and without imposing limitation upon, the claimed invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

FIG. 1A is a schematic top cut-away view of a patch sensor 100 in accordance with one embodiment of the present invention. FIG. 1B is a schematic cross-sectional view of the patch sensor 100 taken along a direction A-A of FIG. 1A. As shown in FIGS. 1A-B, the patch sensor 100 may include: a substrate 102 configured to attach to a host structure; a hoop layer 104; a piezoelectric device 108 for generating and/or receiving signals (more specifically, Lamb waves); a buffer layer 110 for providing mechanical impedance matching and reducing thermal stress mismatch between the substrate 102 and the piezoelectric device 108; two electrical wires 118a-b connected to the piezoelectric device 108; a molding layer 120 for securing the piezoelectric device 108 to the substrate 102; and a cover layer 106 for protecting and sealing the molding layer 120. The piezoelectric device 108 includes: a piezoelectric layer 116; a bottom conductive flake 112 connected to the electrical wire 118b; and a top conductive flake 114 connected to the electrical wire 118a. The piezoelectric device 108 may operate as an actuator (or, equivalently, signal generator) when a pre-designed electric signal is applied through the electric wires 118a-b. Upon application of an electrical signal, the piezoelectric layer 116 may deform to generate Lamb waves. Also, the piezoelectric device 108 may operate as a receiver for sensing vibrational signals, converting the vibrational signals applied to the piezoelectric layer 116 into electric signals and transmitting the electric signals through the wires 118a-b. The wires 118a-b may be a thin ribbon type metallic wire.

The substrate 102 may be attached to a host structure using a structural adhesive, typically a cast thermosetting epoxy, such as butyralthenolic, acrylic polyimide, nitriale phenolic or aramide. The substrate 102 may be an insulation layer for thermal heat and electromagnetic interference protecting the piezoelectric device 108 affixed to it. In some applications, the dielectric substrate 102 may need to cope with a temperature above 250° C. Also it may have a low dielectric constant to minimize signal propagation delay, interconnection capacitance and crosstalk between the piezoelectric device 108 and its host structure, and high impedance to reduce power loss at high frequency.

The substrate 102 may be made of various materials. Kapton® polyimide manufactured by DuPont, Wilmington, Del., may be preferably used for its commonplace while other three materials of Teflon perfluoroalkoxy (PFA), poly p-xylylene (PPX), and polybenzimidazole (PBI), can be used for their specific applications. For example, PFA film may have good dielectric properties and low dielectric loss to be suitable for low voltage and high temperature applications. PPX and PBI may provide stable dielectric strength at high temperatures.

The piezoelectric layer 116 can be made of piezoelectric ceramics, crystals or polymers. A piezoelectric crystal, such as PZN-PT crystal manufactured by TRS Ceramics, Inc., State College, Pa., may be preferably employed in the design of the piezoelectric device 108 due to its high strain energy density and low strain hysteresis. For small size patch sensors, the piezoelectric ceramics, such as PZT ceramics manufactured by Fuji Ceramic Corporation, Tokyo, Japan, or APC International, Ltd., Mackeyville, Pa., may be used for the piezoelectric layer 116. The top and bottom conductive flakes 112 and 114 may be made of metallic material, such as Cr or Au, and applied to the piezoelectric layer 116 by the conventional sputtering process. In FIG. 1B, the piezoelectric device 108 is shown to have only a pair of conductive flakes. However, it should be apparent to those of ordinary skill that the piezoelectric device 108 may have the multiple stacks of conductive flakes having various thicknesses to optimize the performance of the piezoelectric layer 116 in generating/detecting signal waves. The thickness of each flake may be determined by the constraints of thermal and mechanical loads given in a particular host structure that the patch sensor 100 is attached to.

To sustain temperature cycling, each layer of the piezoelectric device 108 may need to have a thermal expansion coefficient similar to those of other layers. Yet, the coefficient of a typical polyimide comprising the substrate 102 may be about $4-6\times10^{-5}$ $K^{-1}$ while that of a typical piezoelectric ceramic/crystal comprising the piezoelectric layer 116 may be about $3\times10^{-6}$ $K^{-1}$. Such thermal expansion mismatch may be a major source of failure of the piezoelectric device 108. The failure of piezoelectric device 108 may require a replacement of the patch sensor 100 from its host structure. As mentioned, the buffer layer 110 may be used to reduce the negative effect of the thermal coefficient mismatch between the piezoelectric layer 116 and the substrate 102.

The buffer layer 110 may be made of conductive polymer or metal, preferably aluminum (Al) with the thermal expansion coefficient of $2\times10^{-5}$ $K^{-1}$. One or more buffer layers made of alumina, silicon or graphite may replace or be added to the buffer layer 110. In one embodiment, the thickness of the buffer layer 110 made of aluminum may be nearly equal to that of the piezoelectric layer 116, which is approximately 0.25 mm including the two conductive flakes 112 and 114 of about 0.05 mm each. In general, the thickness of the buffer layer 110 may be determined by the material property and thickness of its adjacent layers. The buffer layer 110 may provide an enhanced durability against thermal loads and consistency in the twofold function of the piezoelectric device 108. In an alternative embodiment, the piezoelectric device 108 may have another buffer layer applied over the top conductive flake 114.

Another function of the buffer layer 110 may be amplifying signals received by the substrate 102. As Lamb wave signals generated by a patch sensor 100 propagate along a host structure, the intensity of the signals received by another patch sensor 100 attached on the host structure may decrease as the distance between the two patch sensors increases. When a Lamb signal arrives at the location where a patch sensor 100 is located, the substrate 102 may receive the signal. Then, depending on the material and thickness of the buffer layer 110, the intensity of the received signal may be amplified at a specific frequency. Subsequently, the piezoelectric device 108 may convert the amplified signal into electrical signal.

As moisture, mobile ions and hostile environmental condition may degrade the performance and reduce the lifetime of the patch sensor 100, two protective coating layers, a molding layer 120 and a cover layer 106 may be used. The molding layer 120 may be made of epoxy, polyimide or silicone-polyimide by the normal dispensing method. Also, the molding layer 120 may be formed of a low thermal expansion polyimide and deposited over the piezoelectric device 108 and the substrate 102. As passivation of the molding layer 120 does not make a conformal hermetic seal, the cover layer 106 may be deposited on the molding layer 120 to provide a hermitic seal. The cover layer 120 may be made of metal, such as nickel (Ni), chromium (Cr) or silver (Ag), and deposited by a conventional method, such as electrolysis or e-beam evaporation and sputtering. In one embodiment, an additional film of epoxy or polyimide may be coated on the cover layer 106 to provide a protective layer against scratching and cracks.

The hoop layer 104 may be made of dielectric insulating material, such as silicon nitride or glass, and encircle the piezoelectric device 108 mounted on the substrate 102 to prevent the conductive components of the piezoelectric device 108 from electrical shorting.

FIG. 1C is a schematic top view of a piezoelectric device 130, which may be a conventional type known in the art and can be used in place of the piezoelectric device 108. FIG. 1D is a schematic cross-sectional view of the piezoelectric device 130 taken along the direction B-B of FIG. 1D. As shown FIGS. 1C-D, the piezoelectric device 130 includes: a bottom conductive flake 134; a piezoelectric layer 136; a top conductive flake 132 connected to a wire 138b; a connection flake 142 connected to a wire 138a; and a conducting segment 144 for connecting the connection flake 142 to the bottom flake 134. The top conductive flake 132 may be electrically separated from the connection flake 142 by a groove 140.

FIG. 1E is a schematic top cut-away view of a patch sensor 150 in accordance with another embodiment of the present invention. FIG. 1F is a schematic side cross-sectional view of the patch sensor 150 shown in FIG. 1E. As shown in FIGS. 1E-F, the patch sensor 150 may include: a bottom substrate 151; a top substrate 152; a hoop layer 154; a piezoelectric device 156; top and bottom buffer layers 160a-b; two electrical wires 158a-b connected to the piezoelectric device 108. The piezoelectric device 156 includes: a piezoelectric layer 164; a bottom conductive flake 166 connected to the electrical wire 158b; and a top conductive flake 162 connected to the electrical wire 158a. The functions and materials for the components of the patch sensor 150 may be similar to those for their counterparts of the patch sensor 100. Each of the buffer layers 160a-b may include more than one sublayer and each sublayer may be composed of polymer or metal. The top substrate 152 may be made of the same material as that of the substrate 102.

Figures 1G, 1H:
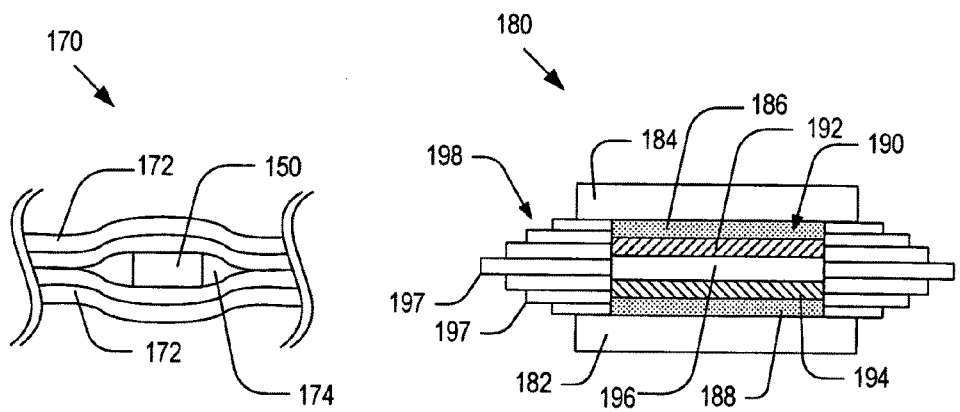
FIG. 1G is a schematic cross-sectional view of a composite laminate including the patch sensor of FIG. 1E.
FIG. 1H is a schematic side cross-sectional view of an alternative embodiment of the patch sensor of FIG. 1E.

The patch sensor 150 may be affixed to a host structure to monitor the structural health conditions. Also, the patch sensor 150 may be incorporated within a laminate. FIG. 1G is a schematic cross-sectional view of a composite laminate 170 having a patch sensor 150 therewithin. As illustrated in FIG. 1G, the host structure includes: a plurality of plies 172; and at least one patch sensor 150 cured with the plurality of plies 172. In one embodiment, the plies 172 may be impregnated with adhesive material, such as epoxy resin, prior to the curing process. During the curing process, the adhesive material from the plies 172 may fill cavities 174. To obviate such accumulation of the adhesive material, the hoop layer 154 may have a configuration to fill the cavity 174.

FIG. 1H is a schematic side cross-sectional view of an alternative embodiment 180 of the patch sensor 150 of FIG. 1E. As illustrated, the patch sensor 180 may include: a bottom substrate 182; a top substrate 184; a hoop layer 198; a piezoelectric device 190; top and bottom buffer layers 192 and 194; and the piezoelectric device 196. For simplicity, a pair of wires connected to the piezoelectric device 190 is not shown in FIG. 1H. The piezoelectric device 190 may include: a piezoelectric layer 196; a bottom conductive flake 194; and a top conductive flake 192. The functions and materials for the components of the patch sensor 180 may be similar to those of their counterparts of the patch sensor 150.

The hoop layer 198 may have one or more sublayers 197 of different dimensions so that the outer contour of the hoop layer 198 may match the geometry of cavity 174. By filling the cavity 174 with sublayers 197, the adhesive material may not be accumulated during the curing process of the laminate 170.

Figure 2A:
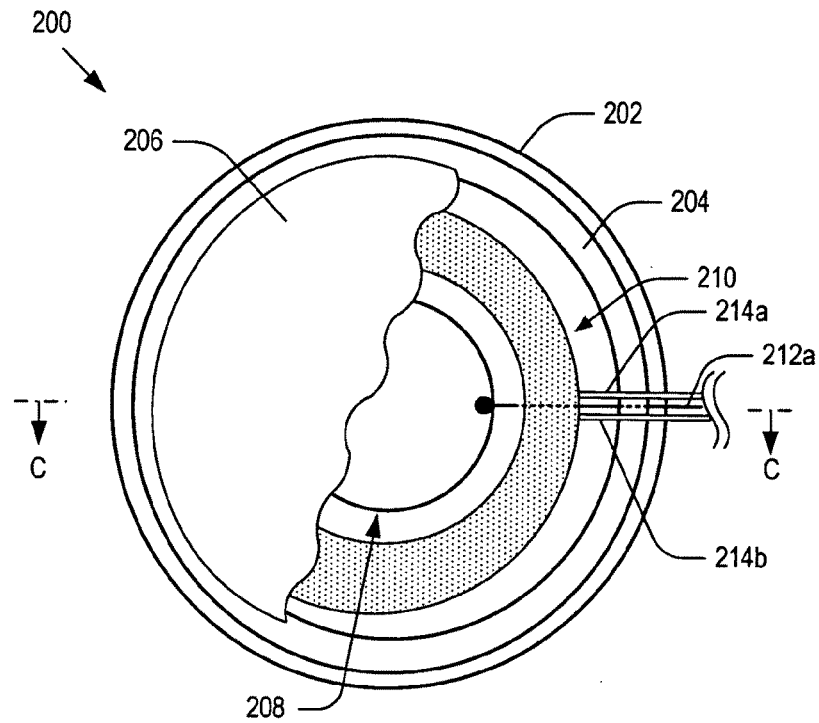
FIG. 2A is a schematic top cut-away view of a hybrid patch sensor in accordance with one embodiment of the present invention.
Figure 2B:
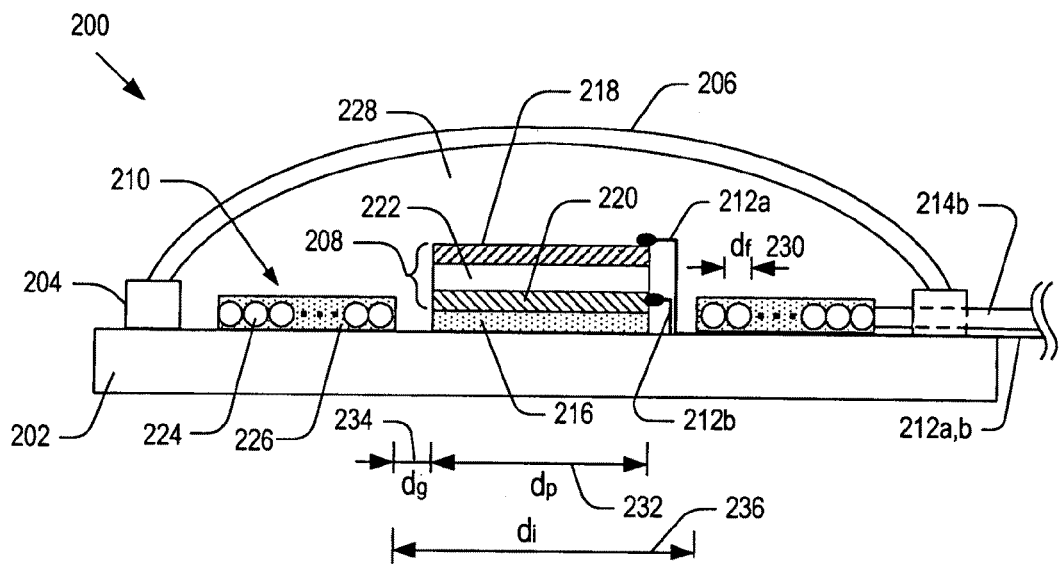
FIG. 2B is a schematic side cross-sectional view of the hybrid patch sensor shown in FIG. 2A.

FIG. 2A is a schematic top cut-away view of a hybrid patch sensor 200 in accordance with one embodiment of the present invention. FIG. 2B is a schematic cross-sectional view of the hybrid patch sensor 200 taken along a direction C-C of FIG. 2A. As shown in FIGS. 2A-B, the hybrid patch sensor 200 may include: a substrate 202 configured to attach to a host structure; a hoop layer 204; a piezoelectric device 208; an optical fiber coil 210 having two ends 214a-b; a buffer layer 216; two electrical wires 212a-b connected to the piezoelectric device 208; a molding layer 228; and a cover layer 206. The piezoelectric device 208 includes: a piezoelectric layer 222; a bottom conductive flake 220 connected to the electrical wire 212b; and a top conductive flake 218 connected to the electrical wire 212a. In an alternative embodiment, the piezoelectric device 208 may be the same as the device 130 of FIG. 1C. The optical fiber coil 210 may include; a rolled optical fiber cable 224; and a coating layer 226. Components of the hybrid patch sensor 200 may be similar to their counterparts of the patch sensor 100.

The optical fiber coil 210 may be a Sagnac interferometer and operate to receive Lamb wave signals. The elastic strain on the surface of a host structure incurred by Lamb wave may be superimposed on the pre-existing strain of the optical fiber cable 224 incurred by bending and tensioning. As a consequence, the amount of frequency/phase change in light traveling through the optical fiber cable 224 may be dependent on the total length of the optical fiber cable 224. In one embodiment, considering its good immunity to electromagnetic interference and vibrational noise, the optical fiber coil 210 may be used as the major sensor while the piezoelectric device 208 can be used as an auxiliary sensor.

The optical fiber coil 210 exploits the principle of Doppler's effect on the frequency of light traveling through the rolled optical fiber cable 224. For each loop of the optical fiber coil 210, the inner side of the optical fiber loop may be under compression while the outer side may be under tension. These compression and tension may generate strain on the optical fiber cable 224. The vibrational displacement or strain of the host structure incurred by Lamb waves may be superimposed on the strain of the optical fiber cable 224. According to a birefringence equation, the reflection angle on the cladding surface of the optical fiber cable 224 may be a function of the strain incurred by the compression and/or tension. Thus, the inner and outer side of each optical fiber loop may make reflection angles different from that of a straight optical fiber, and consequently, the frequency of light may shift from a centered input frequency according to the relative flexural displacement of Lamb wave as light transmits through the optical fiber coil 210.

In one embodiment, the optical fiber coil 210 may include 10 to 30 turns of the optical fiber cable 224 and have a smallest loop diameter 236, $d_l$, of at least 10 mm. There may be a gap 234, $d_g$, between the innermost loop of the optical fiber coil 210 and the outer periphery of the piezoelectric device 208. The gap 234 may depend on the smallest loop diameter 236 and the diameter 232, $d_p$, of the piezoelectric device 208, and be preferably larger than the diameter 232 by about two or three times of the diameter 230, $d_f$, of the optical fiber cable 224.

The coating layer 226 may be comprised of a metallic or polymer material, preferably an epoxy, to increase the sensitivity of the optical fiber coil 210 to the flexural displacement or strain of Lamb waves guided by its host structure. Furthermore, a controlled tensional force can be applied to the optical fiber cable 224 during the rolling process of the optical fiber cable 224 to give additional tensional stress. The coating layer 226 may sustain the internal stress of the rolled optical fiber cable 224 and allow a uniform in-plane displacement relative to the flexural displacement of Lamb wave for each optical loop.

The coating layer 226 may also be comprised of other material, such as polyimide, aluminum, copper, gold or silver. The thickness of the coating layer 226 may range from about 30% to two times of the diameter 230. The coating layer 226 comprised of polymer material may be applied in two ways. In one embodiment, a rolled optic fiber cable 224 may be laid on the substrate 202 and the polymer coating material may be sprayed by a dispenser, such as Biodot spay-coater. In another embodiment, a rolled optic fiber cable 224 may be dipped into a molten bath of the coating material.

Coating layer 226 comprised of metal may be applied by a conventional metallic coating technique, such as magnetron reactive or plasma-assisted sputtering as well as electrolysis. Specially, the zinc oxide can be used as the coating material of the coating layer 226 to provide the piezoelectric characteristic for the coating layer 226. When zinc oxide is applied to top and bottom surfaces of the rolled optical fiber cable 224, the optical fiber coil 210 may contract or expand concentrically in radial direction responding to electrical signals. Furthermore, the coating material of silicon oxide or tantalum oxide can also be used to control the refractive index of the rolled fiber optical cable 224. Silicon oxide or tantalum oxide may be applied using the indirect/direct ion beam-assisted deposition technique or electron beam vapor deposition technique. It is noted that other methods may be used for applying the coating layer 226 to the optical fiber cable 224 without deviating from the present teachings.

The piezoelectric device 208 and the optical fiber coil 210 may be affixed to the substrate 202 using physically setting adhesives instead of common polymers, where the physically setting adhesives may include, but not limited to, butylacrylate-ethylacrylate copolymer, styrene-butadiene-isoprene terpolymer and polyurethane alkyd resin. The adhesive properties of these materials may remain constant during and after the coating process due to the lack of cross-linking in the polymeric structure. Furthermore, those adhesives may be optimized for wetting a wide range of substrate 202 without compromising their sensitivity to different analytes, compared to conventional polymers.

Figure 2C:
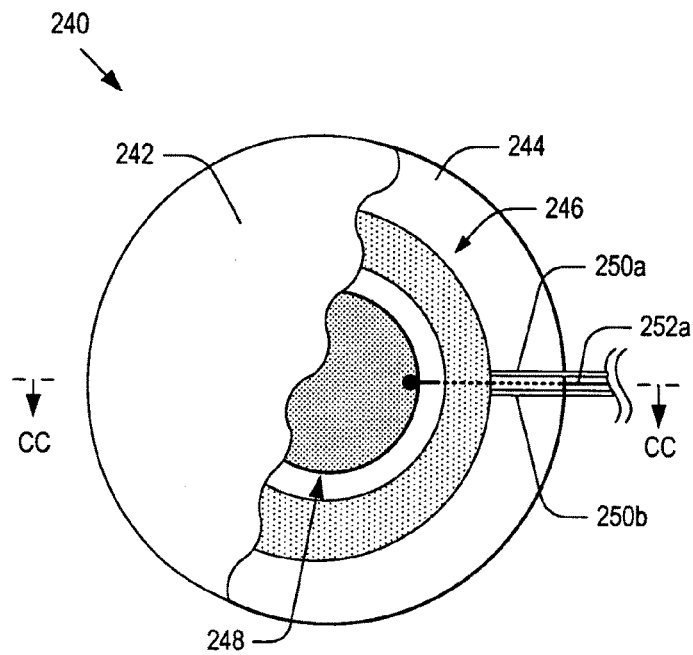
FIG. 2C is a schematic top cut-away view of a hybrid patch sensor in accordance with another embodiment of the present invention.
Figure 2D:
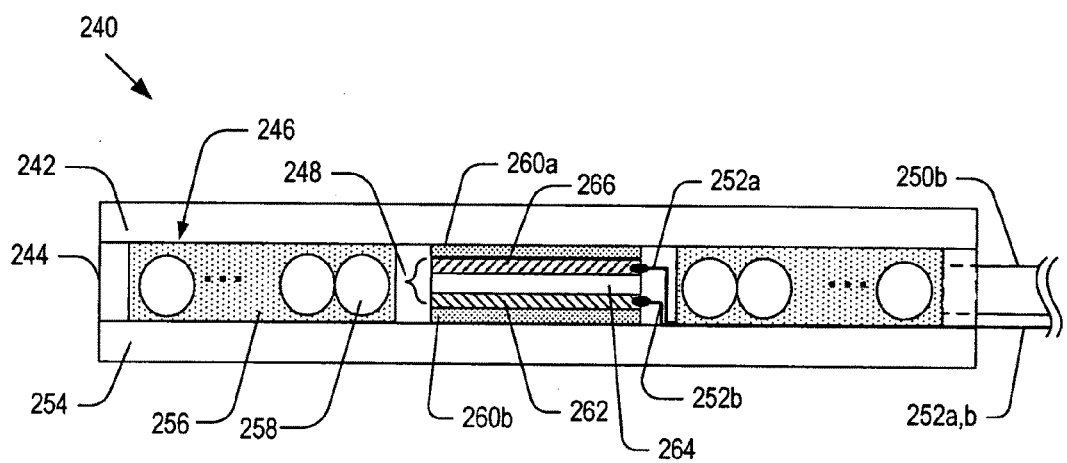
FIG. 2D is a schematic side cross-sectional view of the hybrid patch sensor shown in FIG. 2C.

FIG. 2C is a schematic top cut-away view of a hybrid patch sensor 240 in accordance with another embodiment of the present invention. FIG. 2D is a schematic side cross-sectional view of the hybrid patch sensor 240 shown in FIG. 52C. As shown in FIGS. 2C-D, the hybrid patch sensor 240 may include: a bottom substrate 254; a top substrate 242; a hoop layer 244; a piezoelectric device 248; an optical fiber coil 246 having two ends 250*a-b*; top and bottom buffer layers 260*a-b*; and two electrical wires 252*a-b* connected to the piezoelectric device 248. The piezoelectric device 248 includes: a piezoelectric layer 264; a bottom conductive flake 262 connected to the electrical wire 252*b*; and a top conductive flake 266 connected to the electrical wire 252*a*. The optical fiber coil 246 may include; a rolled optical fiber cable 258; and a coating layer 256. Components of the hybrid patch sensor 240 may be similar to their counterparts of the hybrid patch sensor 200.

As in the case of the patch sensor 150, the hybrid patch sensor 240 may be affixed to a host structure and/or incorporated within a composite laminate. In one embodiment, the hoop layer 244 may be similar to the hoop layer 198 to fill the cavity formed by the patch sensor 240 and the composite laminate.

FIG. 3A a schematic top cut-away view of an optical fiber patch sensor 300 in accordance with one embodiment of the present invention. FIG. 3B a schematic side cross-sectional view of the optical fiber patch sensor 300 taken along the direction D-D of FIG. 3A. As shown in FIGS. 3A-B, the optical fiber patch sensor 300 may include: a substrate 302; a hoop layer 304; an optical fiber coil 308 having two ends 310*a-b*; a molding layer 316; and a cover layer 306. The optical fiber coil 308 may include; a rolled optical fiber cable 312; and a coating layer 314. The material and function of each element of the optical fiber patch sensor 300 may be similar to those of its counterpart of the hybrid patch sensor 200 in FIG. 2A. The diameter 313 of the innermost loop may be determined by the material property of the optic fiber cable 312.

FIG. 3C a schematic top cut-away view of the optical fiber coil 308 contained in the optical fiber patch sensor of FIG. 3A, illustrating a method for rolling the optical fiber cable 312. As shown in FIG. 3C, the outermost loop of the optical fiber coil 308 may start with one end 310*a* while the innermost loop may end with the other end 310*b*. FIG. 3D a schematic top cut-away view of an alternative embodiment 318 of the optical fiber coil 308 shown in FIG. 3C. As shown in FIG. 3D, the optical fiber cable 322 may be folded and rolled in such a manner that the outermost loops may start with both ends 320*a-b*. The rolled optical fiber cable 322 may be covered by a coating layer 319.

Figure 3E:
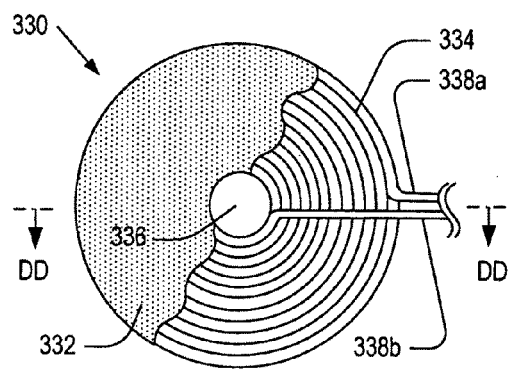
FIGS. 3E-F are schematic top cut-away views of alternative embodiments of the optical fiber coil of FIG. 3C.
Figure 3F:
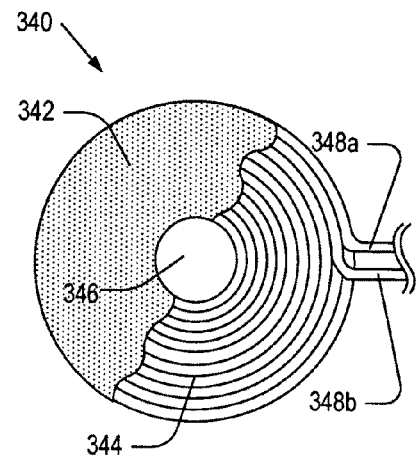
Figure 3G:
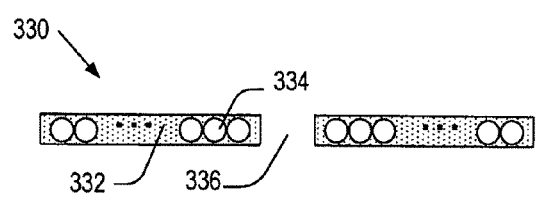
FIG. 3G is a schematic side cross-sectional view of the optical fiber coil of FIG. 3E.

It is noted that the optical fiber coils 308 and 318 show in FIGS. 3C-D may be attached directly to a host structure and used as optical fiber coil sensors. For this reason, hereinafter, the terms "optical fiber coil" and "optical fiber coil sensor" will be used interchangeably. FIGS. 3E-F are alternative embodiments of the optical fiber coil 308. As illustrated in FIG. 3E, the optical fiber coil 330 may include: an optical fiber cable 334 having two ends 338*a-b* and being rolled in the same manner as the cable 312; and a coating layer 332. The coil 330 may have a hole 336 to accommodate a fastener as will be explained later. Likewise, the optical fiber coil 340 in FIG. 3F may include: an optical fiber cable 344 having two ends 348*a-b* and being rolled in the same manner as the cable 322; and a coating layer 342. The coil 340 may have a hole 346 to accommodate a fastener. FIG. 3G is a schematic side cross-sectional view of the optical fiber coil 330 taken along the direction DD of FIG. 3E.

It should be noted that the sensors described in FIG. 3A-G may be incorporated within a laminate in a similar manner as described in FIG. 1G.

Figure 4A:
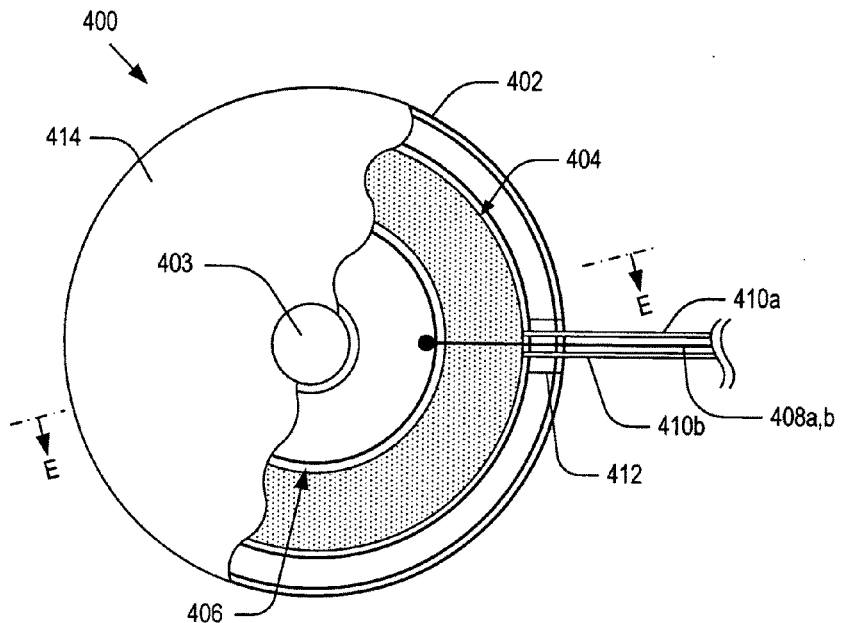
FIG. 4A is a schematic top cut-away view of a diagnostic patch washer in accordance with one embodiment of the present invention.
Figure 4B:
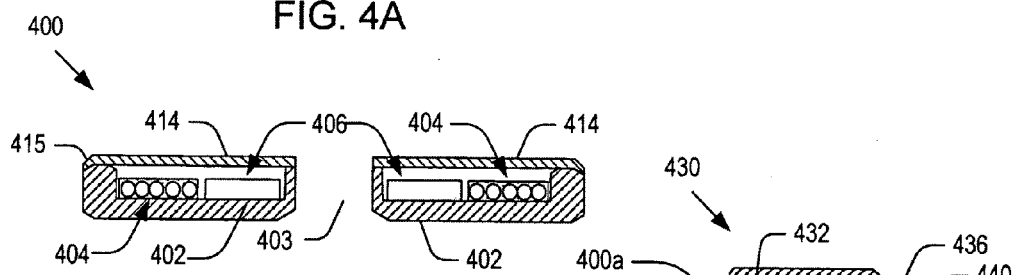
FIG. 4B is a schematic side cross-sectional view of the diagnostic patch washer shown in FIG. 4A.

FIG. 4A a schematic top cut-away view of a diagnostic patch washer 400 in accordance with one embodiment of the present invention. FIG. 4B a schematic side cross-sectional view of the diagnostic patch washer 400 taken along the direction E-E of FIG. 4A. As shown in FIGS. 4A-B, the diagnostic patch washer 400 may include: an optical fiber coil 404 having two ends 410*a-b*; a piezoelectric device 406; a support element 402 for containing the optical fiber coil 404 and the piezoelectric device 406, the coil 404 and the device 406 being affixed to the support element 402 by adhesive material; a pair of electrical wires 408*a-b* connected to the piezoelectric device 406; and a covering disk 414 configured to cover the optical fiber coil 404 and the piezoelectric device 406.

The material and function of the optical fiber coil 404 and the piezoelectric device 406 may be similar to those of the optical fiber coil 210 and the piezoelectric device 208 of the hybrid patch sensor 200. In one embodiment, the piezoelectric device 406 may be similar to the device 130, except that the device 406 has a hole 403. The optical fiber coil 404 and the piezoelectric device 406 may be affixed to the support element 402 using a conventional epoxy. The support element 402 may have a notch 412, through which the ends 410*a-b* of the optical fiber coil 404 and the pair of electrical wires 408*a-b* may pass.

In FIGS. 4A-B, the diagnostic patch washer 400 may operate as an actuator/sensor and have the optical fiber coil 404 and the piezoelectric device 406. In an alternative embodiment, the diagnostic patch washer 400 may operate as a sensor and have the optical fiber coil 404 only. In another alternative embodiment, the diagnostic patch washer 400 may operate as an actuator/sensor and have the piezoelectric device 406 only.

As shown in FIGS. 4A-B, the diagnostic patch washer 400 may have a hollow space 403 to accommodate other fastening device, such as a bolt or rivet. FIG. 4C is a schematic diagram of an exemplary bolt-jointed structure 420 using the diagnostic patch washer 400 in accordance with one embodiment of the present invention. In the bolt-jointed structure 420, a conventional bolt 424, nut 426 and washer 428 may be used to hold a pair of structures 422*a-b*, such as plates. It is well known that structural stress may be concentrated near a bolt-jointed area 429 and prone to structural damages. The diagnostic patch washer 400 may be incorporated in the bolt-joint structure 420 and used to detect such damages.

Figure 4D:
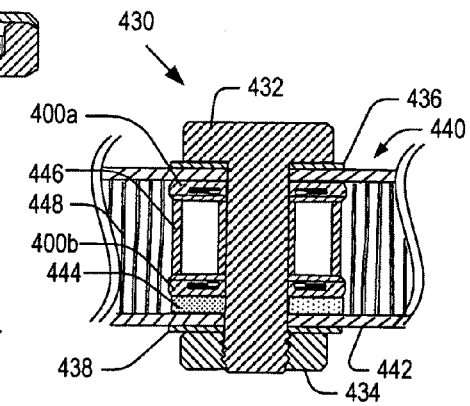
FIG. 4D is a schematic diagram of an exemplary bolt-jointed structure using the diagnostic patch washer of FIG. 4A in accordance with another embodiment of the present invention.
Figure 4C:
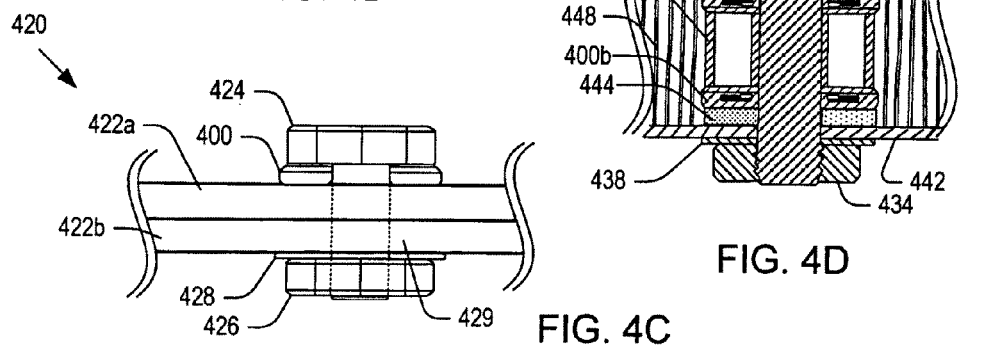
FIG. 4C is a schematic diagram of an exemplary bolt-jointed structure using the diagnostic patch washer of FIG. 4A in accordance with one embodiment of the present invention.

FIG. 4D is a schematic cross-sectional diagram of an exemplary bolt-jointed structure 430 using the diagnostic patch washer 400 in accordance with another embodiment of the present invention. In the bolt-joint structure 430, a conventional bolt 432, nut 434 and a pair of washers 436 and 438 may be used to hold a honeycomb/laminated structure 440. The honeycomb and laminate structure 440 may include a composite laminate layer 422 and a honeycomb portion 448. To detect the structural damages near the bolt-joint area, a pair of diagnostic patch washers 400*a-b* may be inserted within the honeycomb portion 448, as illustrated in FIG. 4D. A sleeve 446 may be required to support the top and bottom patch washers 400*a-b* against the composite laminate layer 442. Also, a thermal-protection circular disk 444 may be inserted between the composite laminate layer 422 and the diagnostic patch washer 400*b* to protect the washer 400*b* from destructive heat transfer.

As shown in FIG. 4B, the outer perimeter 415 of the covering disk 414 may have a slant angle to form a locking mechanism, which can keep optical fiber coil 404 and the piezoelectric device 406 from excessive contact load by the torque applied to the bolt 424 and nut 426.

FIG. 5A is a schematic diagram of an interrogation system 500 including a sensor/actuator device in accordance with one embodiment of the present invention. As shown in FIG. 5A, the system 500 may include: a sensor/actuator device 502 for generating and/or receiving Lamb wave signals; a two-conductor electrical wire 516; a conditioner 508 for processing signals received by the device 502; analog-to-digital (A/D) converter 504 for converting analog signals to digital signals; a computer 514 for managing entire elements of the system 500; an amplifier 506; a waveform generator 510 for converting digital signals into the analog Lamb wave signals; and a relay switch array module 512 configured to switch connections between the device 502 and the computer 514. In general, more than one device 502 may be connected to the relay switch 512.

The device 502 may be one of the sensors described in FIGS. 1A-2D and FIGS. 4A-D that may include a piezoelectric device for generating Lamb waves 517 and receiving Lamb waves generated by other devices. To generate Lamb waves 517, a waveform generator 510 may receive the digital signals of the excitation waveforms from computer 514 (more specifically, an analog output card included in the computer 514) through the relay switch array module 512. In one embodiment, the waveform generator 510 may be an analog output card.

The relay switch array module 512 may be a conventional plug-in relay board. As a "cross-talks" linker between the actuators and sensors, the relay switches included in the relay switch array module 512 may be coordinated by the microprocessor of the computer 514 to select each relay switch in a specific sequencing order. In one embodiment, analog signals generated by the waveform generator 510 may be sent to other actuator(s) through a branching electric wire 515.

The device 502 may function as a sensor for receiving Lamb waves. The received signals may be sent to the conditioner 508 that may adjust the signal voltage and filter electrical noise to select meaningful signals within an appropriate frequency bandwidth. Then, the filtered signal may be sent to the analog-to-digital converter 504, which may be a digital input card. The digital signals from the analog-to-digital converter 504 may be transmitted through the relay switch array module 512 to the computer 514 for further analysis.

FIG. 5B is a schematic diagram of an interrogation system 520 including a sensor in accordance with another embodiment of the present invention. The system 520 may include: a sensor 522 having an optical fiber coil; optical fiber cable 525 for connections; a laser source 528 for providing a carrier input signal; a pair of modulators 526 and 534; an acoustical optic modulator (AOM) 530; a pair of coupler 524 and 532; a photo detector 536 for sensing the light signal transmitted through the optical fiber cable 525; an A/D converter 538; a relay switch 540; and a computer 542. The sensor 522 may be one of the sensors described in FIGS. 2A-4D that may include an optical fiber coil. In one embodiment, the coupler 524 may couple the optical fiber cable 525 to another optical fiber 527 that may be connected to another sensor 523.

The sensor 522, more specifically the optic fiber coil included in the sensor 522, may operate as a laser Doppler velocitimeter (LDV). The laser source 528, preferably a diode laser, may emit an input carrier light signal to the modulator 526. The modulator 526 may be a heterodyne modulator and split the carrier input signal into two signals; one for the sensor 522 and the other for AOM 530. The sensor 522 may shift the input carrier signal by a Doppler's frequency corresponding to Lamb wave signals and transmit it to the modulator 534, where the modulator 534 may be a heterodyne synchronizer. The modulator 534 may demodulate the transmitted light to remove the carrier frequency of light. The photo detector 536, preferably a photo diode, may convert the demodulated light signal into an electrical signal. Then, the A/D converter 538 may digitize the electrical signal and transmit to the computer 542 via the relay switch array module 540. In one embodiment, the coupler 532 may couple an optical fiber cable 546 connected to another sensor 544.

Figure 6A:
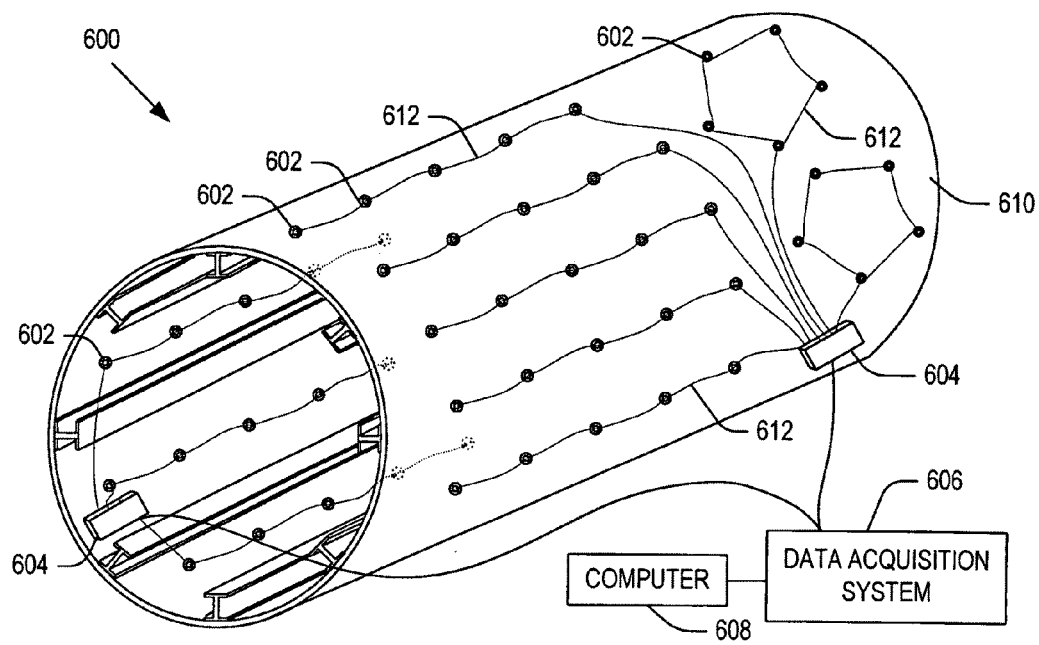
FIG. 6A is a schematic diagram of a diagnostic network patch system applied to a host structure in accordance with one embodiment of the present invention.

FIG. 6A is a schematic diagram of a diagnostic network patch system (DNP) 600 applied to a host structure 610 in accordance with one embodiment of the present invention. As illustrated in FIG. 6A, the system 600 may include: patches 602; transmission links 612; at least one bridge box 604 connected to the transmission links 612; a data acquisition system 606; and a computer 608 for managing the DNP system 600. The patches 602 may be a device 502 or a sensor 522, where the type of transmission links 612 may be determined by the type of the patches 602 and include electrical wires, optical fiber cables, or both. Typically, the host structure 610 may be made of composite or metallic material.

Transmission links 612 may be terminated at the bridge box 604. The bridge box 604 may connect the patches 602 to admit signals from an external waveform generator 510 and to send received signals to an external A/D converter 504. The bridge box 604 may be connected through an electrical/optical cable and can contain an electronic conditioner 508 for conditioning actuating signals, filtering received signals, and converting fiber optic signals to electrical signals. Using the relay switch array module 512, the data acquisition system 606 coupled to the bridge box 604 can relay the patches 602 and multiplex received signals from the patches 602 into the channels in a predetermined sequence order.

It is well known that the generation and detection of Lamb waves is influenced by the locations of actuators and sensors on a host structure. Thus, the patches 602 should be properly paired in a network configuration to maximize the usage of Lamb waves for damage identification.

Figure 6B:
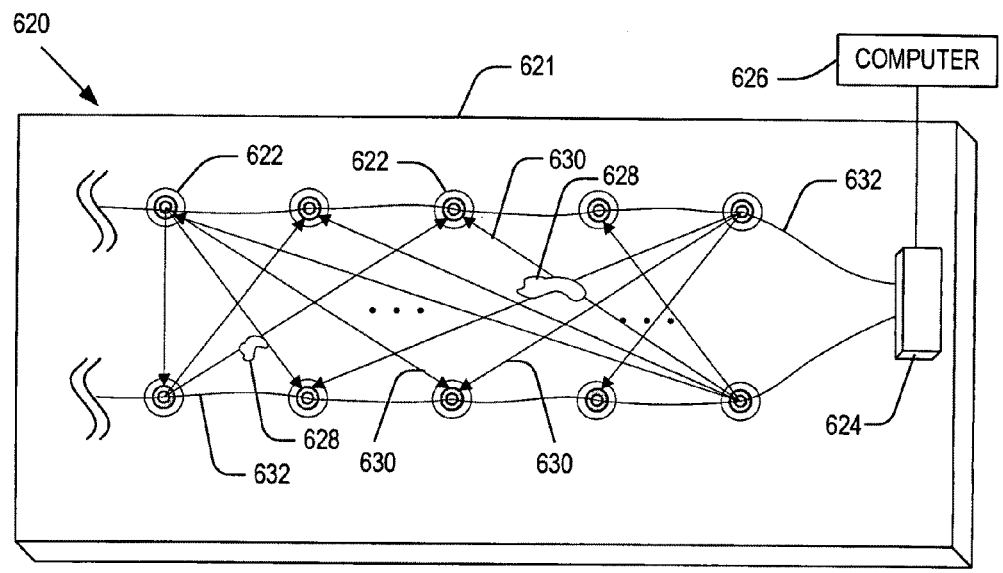
FIG. 6B is a schematic diagram of a diagnostic network patch system having a strip network configuration in accordance with one embodiment of the present invention.

FIG. 6B is a schematic diagram of a diagnostic network patch system 620 having a strip network configuration in accordance with one embodiment of the present invention. As shown in FIG. 6B, the system 620 may be applied to a host structure 621 and include: patches 622; a bridge box 624 connected to a computer 626; and transmission links 632. The patches 622 may be a device 502 or a sensor 522, where the type of the patches 622 may determine the type of transmission links 632. The transmission links 632 may be electrical wires, optical fiber cables, or both.

The computer 626 may coordinate the operation of patches 622 such that they may function as actuators and/or sensors. Arrows 630 represents the propagation of Lamb waves generated by patches 622. In general, defects 628 in the host structure 621 may affect the transmission pattern in the terms of wave scattering, diffraction, and transmission loss of Lamb waves. The defects 628 may include damages, crack and delamination of composite structures, etc. The defects 628 may be monitored by detecting the changes in transmission pattern of Lamb waves captured by the patches 622.

The network configuration of DNP system is important in Lamb-wave based structural health monitoring systems. In the network configuration of DNP system 620, the wave-ray communication paths should be uniformly randomized. Uniformity of the communication paths and distance between the patches 622 can determine the smallest detectible size of defects 628 in the host structure 621. An optimized network configuration with appropriate patch arrangement may enhance the accuracy of the damage identification without increasing the number of the patches 622.

Figure 6C:
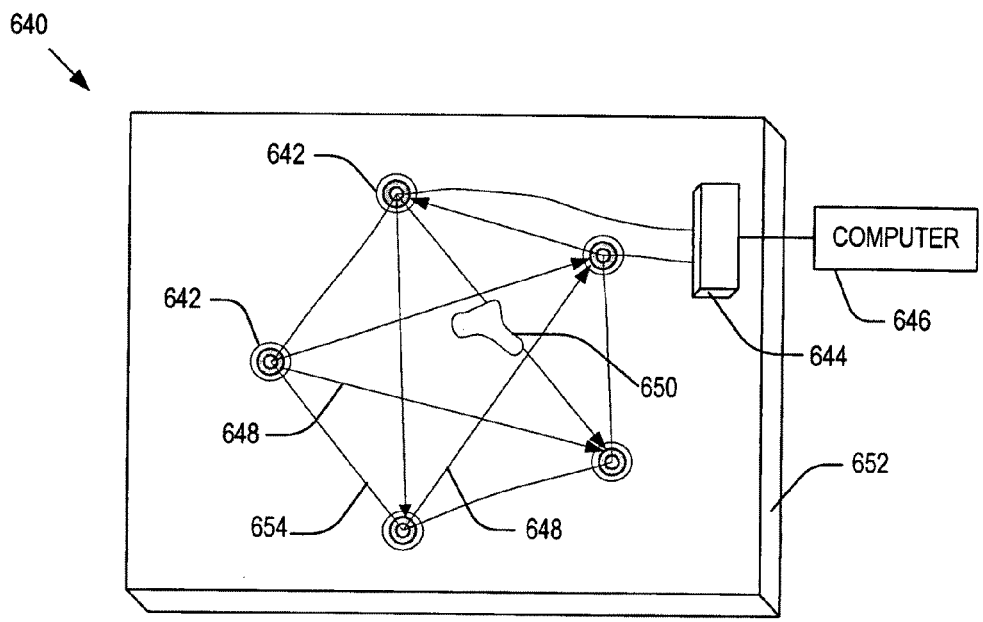
FIG. 6C is a schematic diagram of a diagnostic network patch system having a pentagon network configuration in accordance with one embodiment of the present invention.

Another configuration for building up wave 'cross-talk' paths between patches may be a pentagonal network as shown in FIG. 6C. FIG. 6C is a schematic diagram of a diagnostic network patch system 640 having a pentagon network configuration in accordance with another embodiment of the present invention. The system 640 may be applied to a host structure 652 and may include: patches 642; a bridge box 644 connected to a computer 646; and transmission links 654. The patches 642 may be a device 502 or a sensor 522. As in the system 630, the patches 642 may detect a defect 650 by sending or receiving Lamb waves indicated by the arrows 648.

Figure 6D:
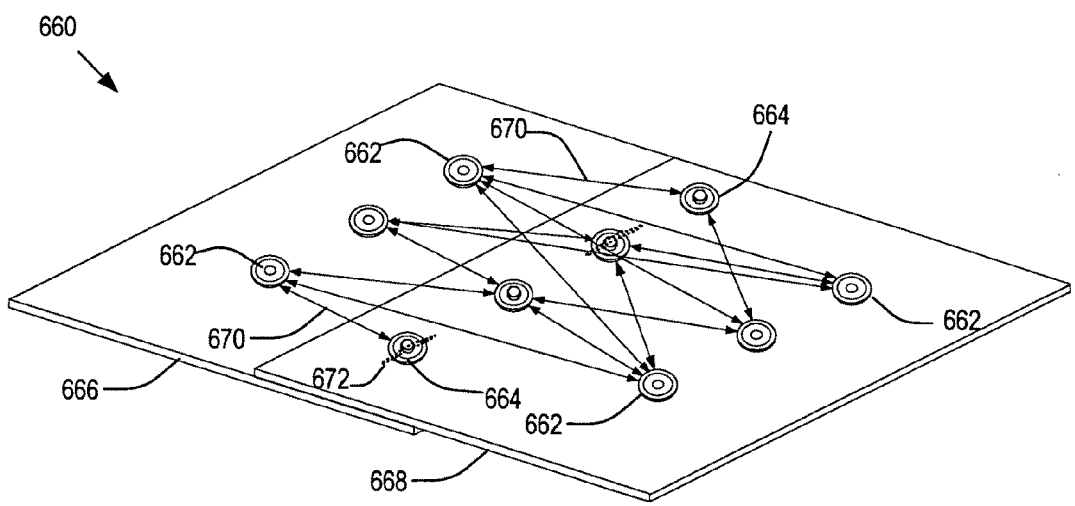
FIG. 6D is a schematic perspective view of a diagnostic network patch system incorporated into rivet/bolt-jointed composite laminates in accordance with one embodiment of the present invention.

FIG. 6D is a schematic perspective view of a diagnostic network patch system 660 incorporated into rivet/bolt-jointed composite laminates 666 and 668 in accordance with another embodiment of the present invention. As illustrated in FIG. 6D, the system 660 may include: patches 662; and diagnostic patch washers 664, each washer being coupled with a pair of bolt and nut. For simplicity, a bridge box and transmission links are not shown in FIG. 6D. The patches 662 may be a device 502 or a sensor 522. In the system 660, the patches 662 and diagnostic patch washers 664 may detect the defects 672 by sending or receiving Lamb waves as indicated by arrows 670. Typically, the defects 672 may develop near the holes for the fasteners. The diagnostic patch washers 664 may communicate with other neighborhood diagnostic patches 662 that may be arranged in a strip network configuration, as shown in FIG. 6D. In one embodiment, the optical fiber coil sensors 330 and 340 may be used in place of the diagnostic patch washers 664.

Figure 6E:
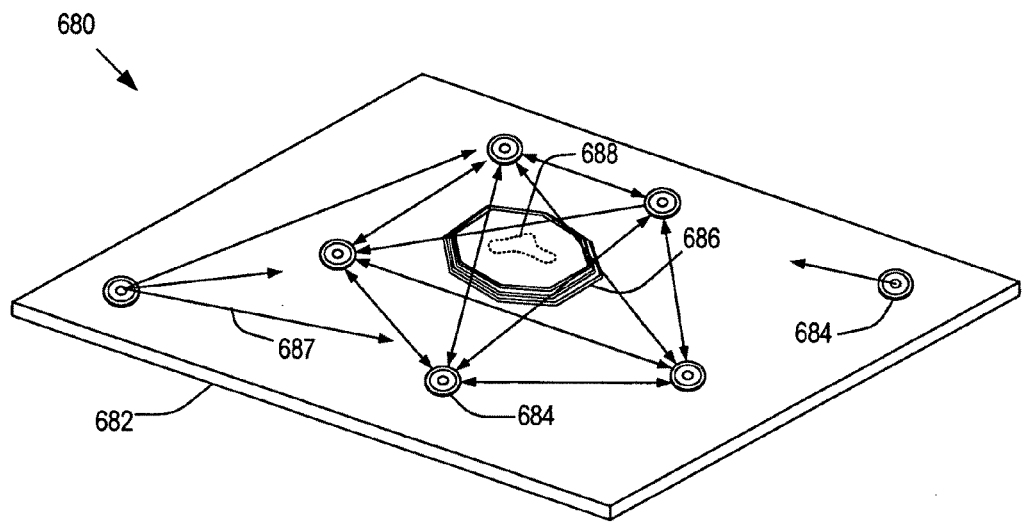
FIG. 6E is a schematic perspective view of a diagnostic network patch system incorporated into a composite laminate repaired with a bonding patch in accordance with another embodiment of the present invention.

FIG. 6E is a schematic perspective view of a diagnostic network patch system 680 applied to a composite laminate 682 that may be repaired with a bonding patch 686 in accordance with one embodiment of the present invention. As illustrated in FIG. 6E, the system 680 may include patches 684 that may be a device 502 or a sensor 522. For simplicity, a bridge box and transmission links are not shown in FIG. 6E. In the system 680, the patches 684 may detect the defects 688 located between the repair patch 686 and the composite laminate 682 by sending or receiving Lamb waves as indicated by arrows 687.

Figure 6F:
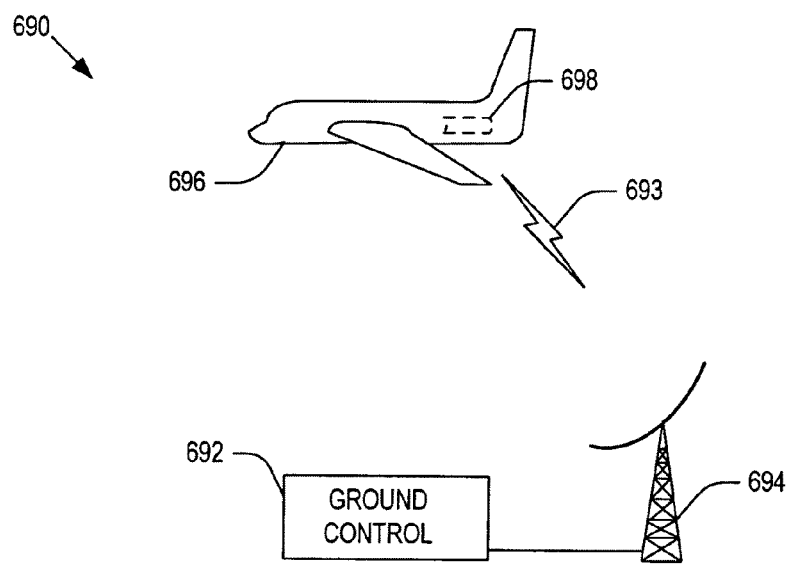
FIG. 6F is a schematic diagram illustrating an embodiment of a wireless communication system that controls a remote diagnostic network patch system in accordance with one embodiment of the present invention.

FIG. 6F is a schematic diagram illustrating an embodiment of a wireless data communication system 690 that controls a remote diagnostic network patch system in accordance with one embodiment of the present invention. As illustrated in FIG. 6F, the system 690 includes: a bridge box 698; and a ground communication system 694 that may be operated by a ground control 692. The bridge box 698 may be coupled to a diagnostic network patch system implemented to a host structure, such as an airplane 696, that may require extensive structural health monitoring.

The bridge box 698 may operate in two ways. In one embodiment, the bridge box 698 may operate as a signal emitter. In this embodiment, the bridge box 698 may comprise micro miniature transducers and a microprocessor of a RF telemetry system that may send the structural health monitoring information to the ground communication system 694 via wireless signals 693. In another embodiment, the bridge box 698 may operate as a receiver of electromagnetic waves. In this embodiment, the bridge box 698 may comprise an assembly for receiving power from the ground communication system 694 via wireless signals 693, where the received power may be used to operate a DNP system applied to the structure 696. The assembly may include a micromachined silicon substrate that has stimulating electrodes, complementary metal oxide semiconductor (CMOS), bipolar power regulation circuitry, hybrid chip capacitors, and receiving antenna coils.

The structure of the bridge box 698 may be similar to the outer layer of the host structure 696. In one embodiment, the bridge box 698 may have a multilayered honeycomb sandwich structure, where a plurality of micro strip antennas are embedded in the outer faceplate of the multilayered honeycomb sandwich structure and operate as conformal load-bearing antennas. The multilayered honeycomb sandwich structure may comprise a honeycomb core and multilayer dielectric laminates made of organic and/or inorganic materials, such as e-glass/epoxy, Kevlar/epoxy, graphite/epoxy, aluminum or steel. As the integrated micro-machining technology evolves rapidly, the size and production cost of the micro strip antennas may be reduced further, which may translate to savings of operational/production costs of the bridge box 698 without compromising its performance.

The scope of the invention is not intended to limit to the use of the standard Wireless Application Protocol (WAP) and the wireless markup languages for a wireless structural health monitoring system. With a mobile Internet toolkit, the application system can build a secure site to which structural condition monitoring or infrastructure management can be correctly accessed by a WAP-enable cell phone, a Pocket PC with a HTML browser, or other HTML-enabled devices.

Figure 7A:
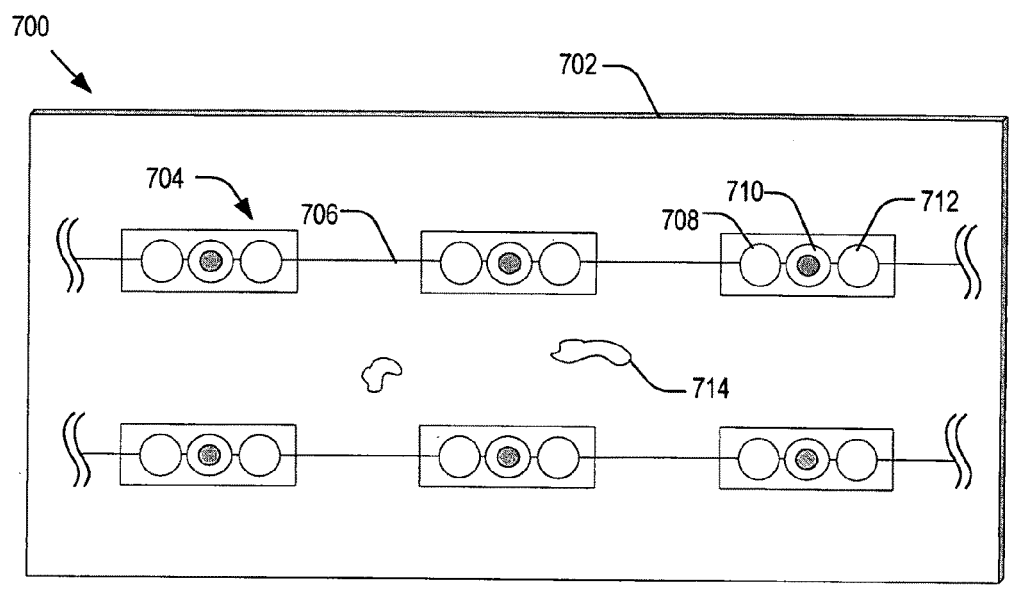
FIG. 7A is a schematic diagram of a diagnostic network patch system having clustered sensors in a strip network configuration in accordance with one embodiment of the present invention.

As a microphone array may be used to find the direction of a moving source, a clustered sensor array may be used to find damaged locations by measuring the difference in time of signal arrivals. FIG. 7A is a schematic diagram of a diagnostic network patch system 700 having clustered sensors in a strip network configuration in accordance with one embodiment of the present invention. As illustrated in FIG. 7A, the system 700 may be applied to a host structure 702 and include clustered sensors 704 and transmission links 706. Each clustered sensor 704 includes two receivers 708 and 712 and one actuator/receiver device 710. Each of the receivers 708 and 712 may be one of the sensors described in FIGS. 1A-4D, while the actuator/receiver device 710 may be one of the sensors described in FIGS. 1A-2D and FIGS. 4A-D and have a piezoelectric device for generating Lamb waves. When the actuator/receiver 710 of a clustered sensor 704 sends Lamb waves, the neighboring clustered sensors 704 may receive the Lamb waves using all three elements, i.e., the actuator/receiver device 710 and receivers 708 and 712. By using all three elements as a receiver unit, each clustered sensor 704 can receive more refined Lamb wave signals. Also, by measuring the difference in time-of-arrivals between the three elements, the direction of the defect 714 may be located with enhanced accuracy.

Figure 7B:
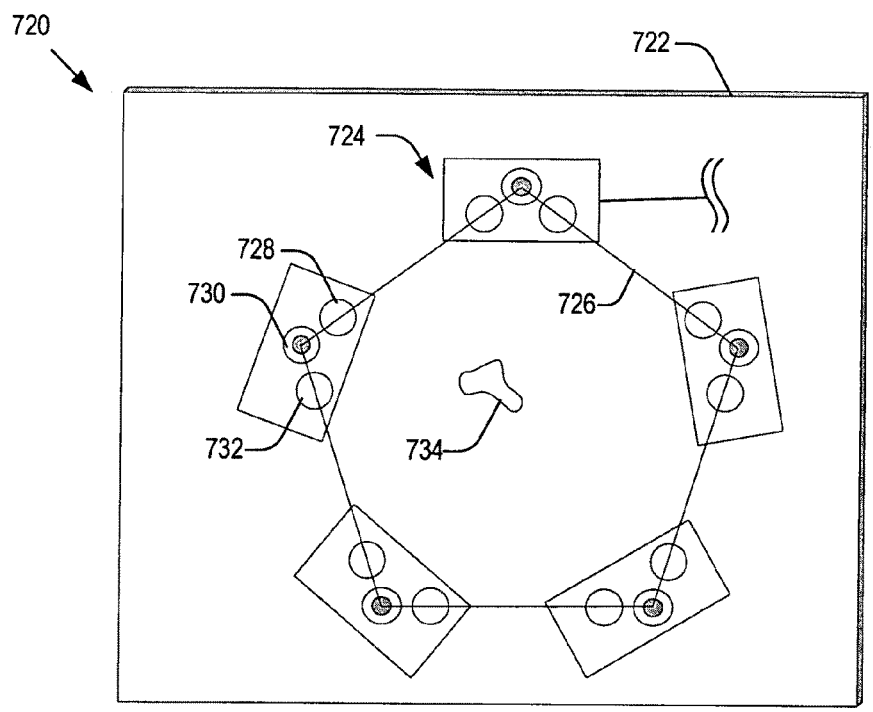
FIG. 7B is a schematic diagram of a diagnostic network patch system having clustered sensors in a pentagonal network configuration in accordance with another embodiment of the present invention.

FIG. 7B is a schematic diagram of a diagnostic network patch system 720 having clustered sensors in a pentagonal network configuration in accordance with another embodiment of the present invention. As illustrated in FIG. 7B, the system 720 may be applied to a host structure 722 to detect a defect 734 and include clustered sensors 724 and transmission links 726. Each clustered sensor 724 may be similar to the clustered sensor 704.

Figure 8A:
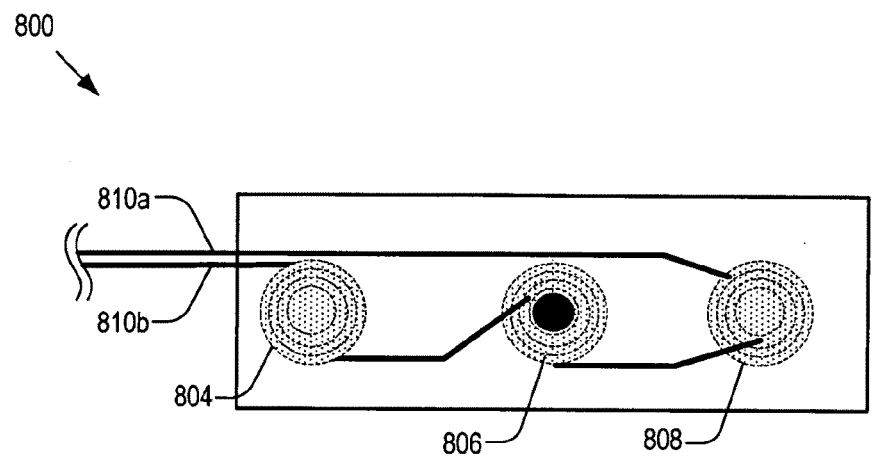
FIG. 8A is a schematic diagram of a clustered sensor having optical fiber coils in a serial connection in accordance with one embodiment of the present invention.

FIG. 8A shows a schematic diagram of a clustered sensor 800 having optical fiber coils in a serial connection in accordance with one embodiment of the present invention. The clustered sensor 800 may be similar to the clustered sensor 704 in FIG. 7A and include two sensors 804 and 808 and an actuator/sensor 806. In this configuration, an input signal may enter the sensor through one end 810a and the output signal from the other end 810b may be a sum of the input signal and contribution of the three sensors 804, 806 and 808. In one embodiment, the signal from each sensor may be separated from others using a wavelength-based de-multiplex techniques.

Figure 8B:
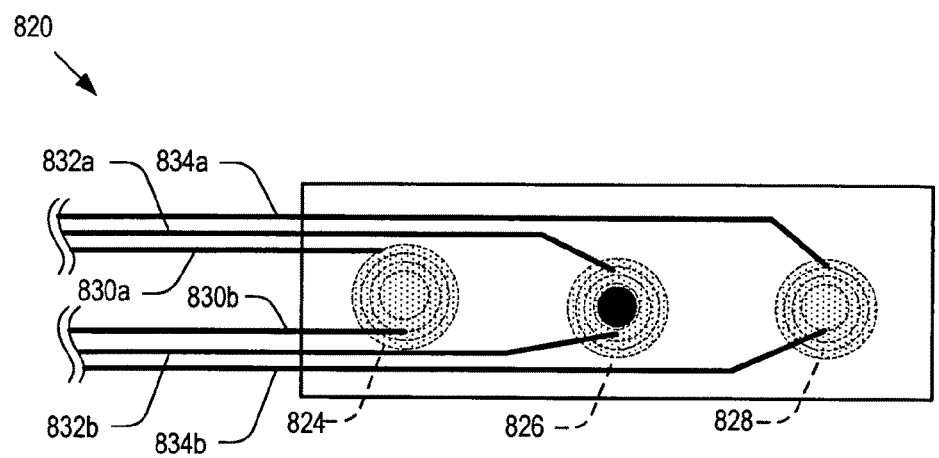
FIG. 8B is a schematic diagram of a clustered sensor having optical fiber coils in a parallel connection in accordance with another embodiment of the present invention.

FIG. 8B a schematic diagram of a clustered sensor 820 having optical fiber coils in a parallel connection in accordance with one embodiment of the present invention. The clustered sensor 820 may be similar to the clustered sensor 704 in FIG. 7A and include two sensors 824 and 828 and an actuator/sensor 826. In this configuration, input signals may enter the three sensors through three end 830a, 832a and 834a, respectively, while output signals from the other ends 830b, 832b and 834b may be a sum of the input signal and contribution of the three sensors 824, 826 and 828, respectively.

It is noted that, in FIGS. 8A-B, the sensors 804, 808, 824 and 828 have been illustrated as optical fiber coil sensors 308. However, it should apparent to those of ordinary skill in the art that each of the sensors 804, 808, 824 and 828 may be one of the sensors described in FIGS. 1A-4D, while each of the middle sensors 806 and 826 may be one of the sensors described in 1A-2D and FIGS. 4A-D and have a piezoelectric device for generating Lamb waves. Also, the clustered sensors 800 and 820 may be incorporated within a composite laminate in the same manner as described in FIG. 1G.

Figure 9:
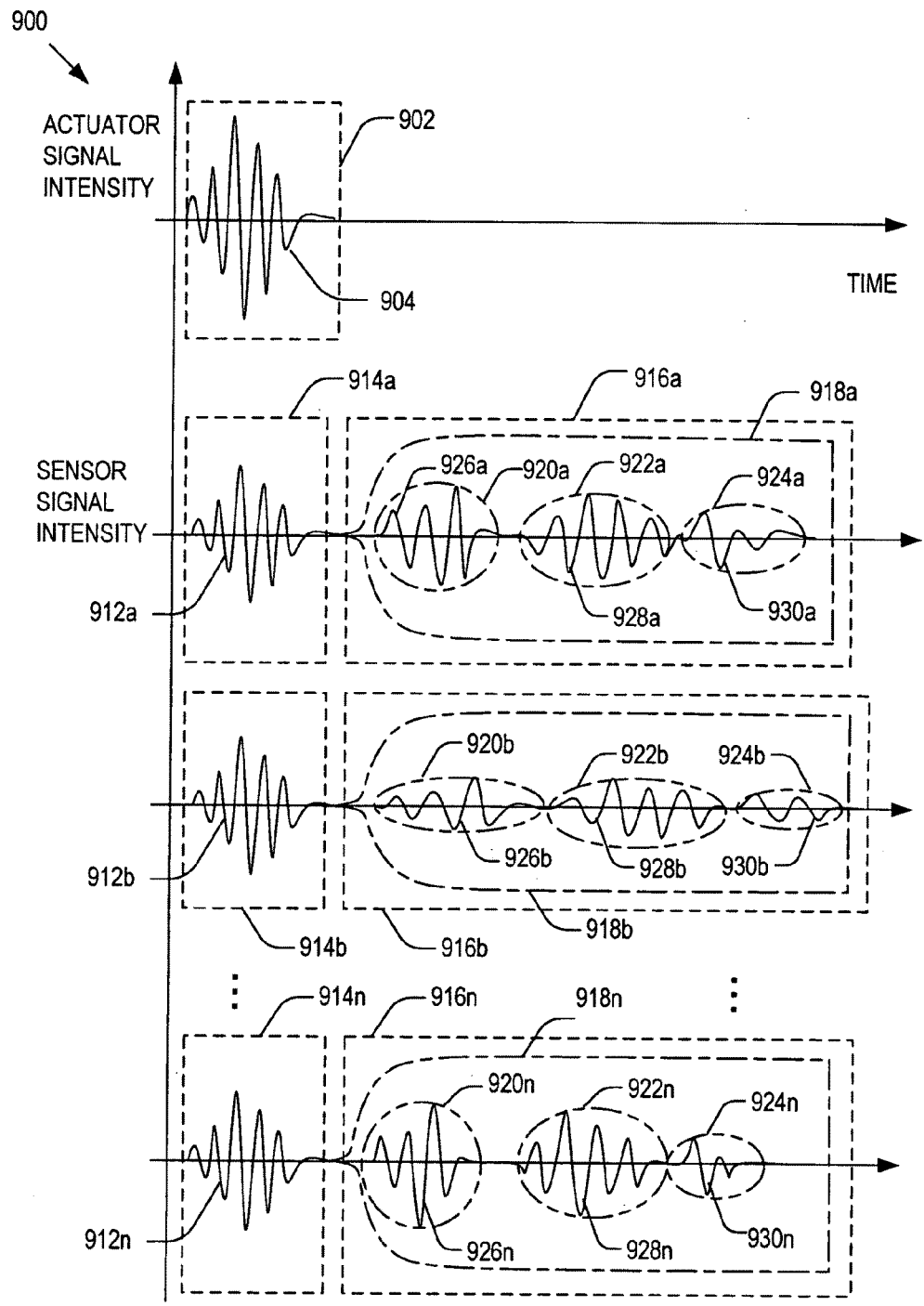
FIG. 9 is a plot of actuator and sensor signals in accordance with one embodiment of the present invention.

FIG. 9 shows a plot 900 of actuator and sensor signals in accordance with one embodiment of the present invention. To generate Lamb waves, an actuator signal 904 may be applied to an actuator, such as a patch sensor 100. The actuator signal 904 may be a toneburst signal that has several wave peaks with the highest amplitude in the mid of waveform and has a spectrum energy of narrow frequency bandwidth. The actuator signal 904 may be designed by the use of Hanning function on various waveforms and have its central frequency within 0.01 MHz to 1.0 MHz. When the actuator receives the actuator signal 904, it may generate Lamb waves having a specific excitation frequency.

Signals 912a-n may represent sensor signals received by sensors. As can be noticed, each signal 912 may have wave packets 926, 928 and 930 separated by signal extracting windows (or, equivalently envelops) 920, 922 and 924, respectively. These wave packets 926, 928 and 930 may have different frequencies due to the dispersion modes at the sensor location. It is noted that the signal partitioning windows 916 have been applied to identify Lamb-wave signal from each sensor signal. The wave packets 926, 928 and 930 correspond to a fundamental symmetric mode $S_0$, a reflected mode $S_{0\_ref}$ and a fundamental antisymmetric mode $A_0$, respectively. The reflected mode $S_{0\_ref}$ may represent the reflection of Lamb waves from a host structure boundary. A basic shear mode, $S_0'$, and other higher modes can be observed. However, they are not shown in FIG. 9 for simplicity.

Portions 914 of sensor signals 912 may be electrical noise due to the toneburst actuator signal 904. To separate the portions 914 from the rest of sensor signals 912, masking windows 916, which may be a sigmoid function delayed in the time period of actuation, may be applied to sensor signals 912 as threshold functions. Then, moving wave-envelope windows 920, 922 and 924 along the time history of each sensor signal may be employed to extract the wave packets 926, 928 and 930 from the sensor signal of 912. The wave packets 926, 928 and 930 may be the sensor part of the sensor signal 912. The envelope windows 920, 922 and 924 may be determined by applying a hill-climbing algorithm that searches for peaks and valleys of the sensor signals 912 and interpolating the searched data point in time axis. The magnitude and position of each data point in the wave signal may be stored if the magnitude of the closest neighborhood data points are less than that of the current data point until the comparison of wave magnitude in the forward and backward direction continues to all the data points of the wave signal. Once wave envelopes 918 are obtained, each envelope may break into sub envelope windows 920, 922 and 924 with time spans corresponding to those of Lamb-wave modes. The sub envelop windows 920, 922 and 924 may be applied to extract wave packets 926, 928 and 930 by moving along the entire time history of each measured sensor signal 912.

Figure 10:
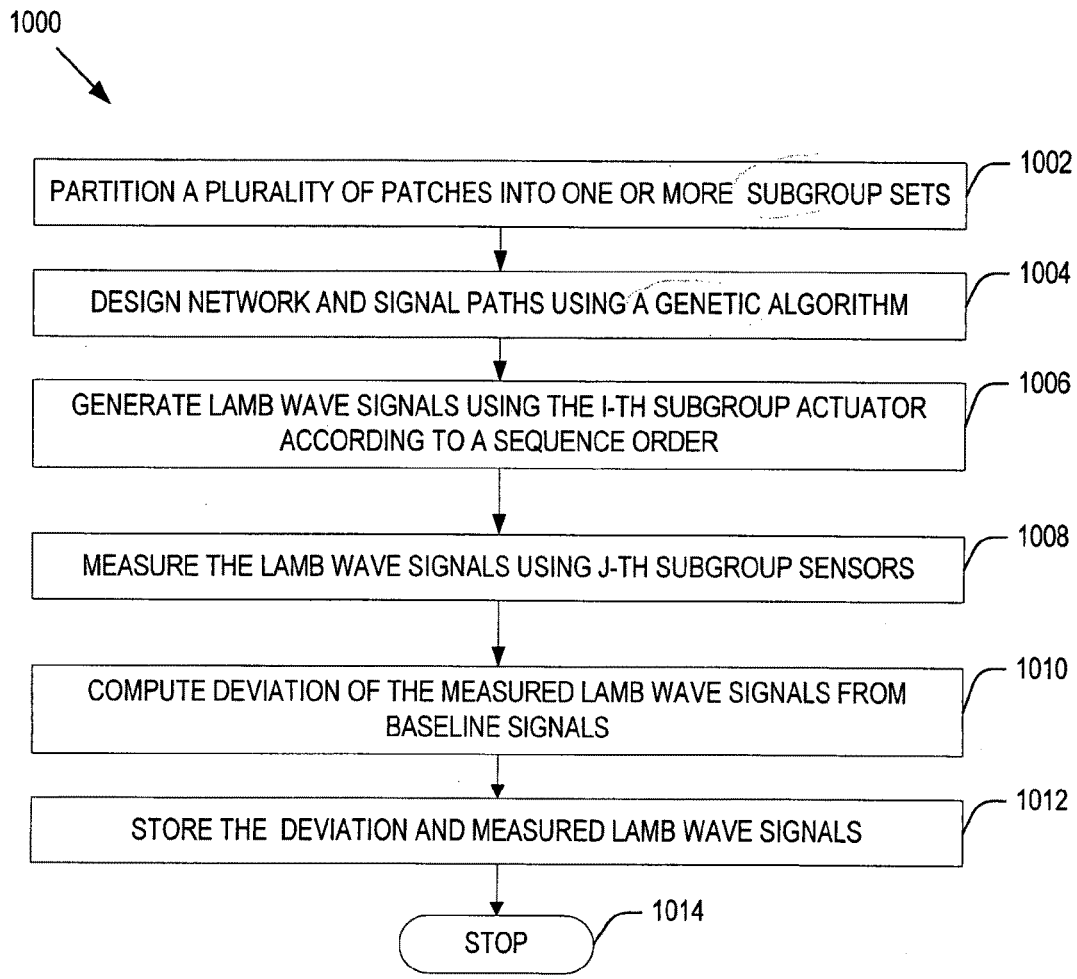
FIG. 10 is a flow chart illustrating exemplary procedures of an interrogation module in accordance with one embodiment of the present invention.
Figure 11A:
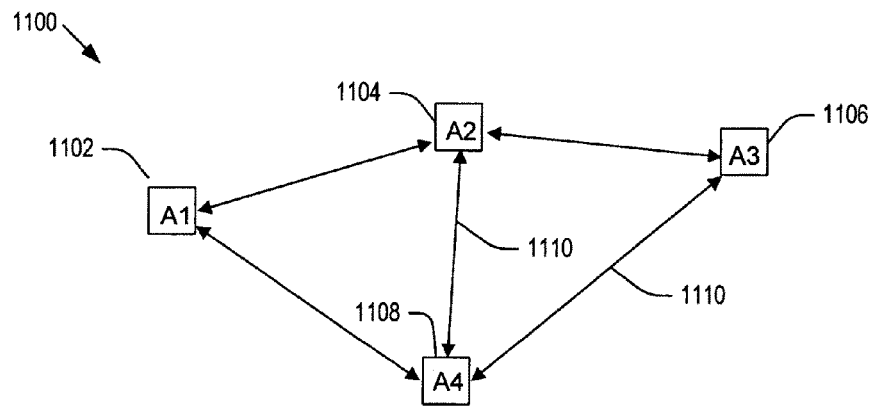
FIG. 11A is a schematic diagram of an exemplary actuator network architecture including subgroups in accordance with one embodiment of the present invention.

Upon completion of applying a DNP system to a host structure, a structural health monitoring software may start processing the DNP system, where the monitoring software may comprise interrogation, processing, classification and prognosis modules. FIG. 10 is a flow chart 1000 illustrating exemplary procedures of the interrogation module in accordance with one embodiment of the present invention. The interrogating module may find damages, identify impacts and monitor the curing and repaired-boning-patch performance of the host structures. In step 1002, the interrogation module may partition the diagnostic patches of the DNP system into subgroup sets, and designate one actuator in each of the subgroups. It is noted that each of the diagnostic patches may function as an actuator at one point in time, and thereafter the same patch may be switched to function as a sensor. FIG. 11A illustrates an example of actuator network architecture 1100 that may include subgroups partitioned by the interrogation module in accordance with one embodiment of the present invention. As each of the actuators 1102, 1104, 1106 and 1108 may also function as a sensor, various combinations of subgroups can be formed of those actuators. Arrows 1110 represent the propagation of Lamb wave signals between actuators 1102, 1104, 1106 and 1108. Table 1 shows the possible subgroups, where each group has one actuator. For example, subgroup 1 has one actuator A1 1102 and two sensors A2 1104 and A4 1108.

TABLE 1

Subgroups made of four patches in FIG. 11A

| Subgroup number | actuator | sensors |
| --- | --- | --- |
| 1 | A1 | A2, A4 |
| 2 | A2 | A1, A3, A4 |
| 3 | A3 | A2, A4 |
| 4 | A4 | A1, A2, A3 |

Figure 11B:
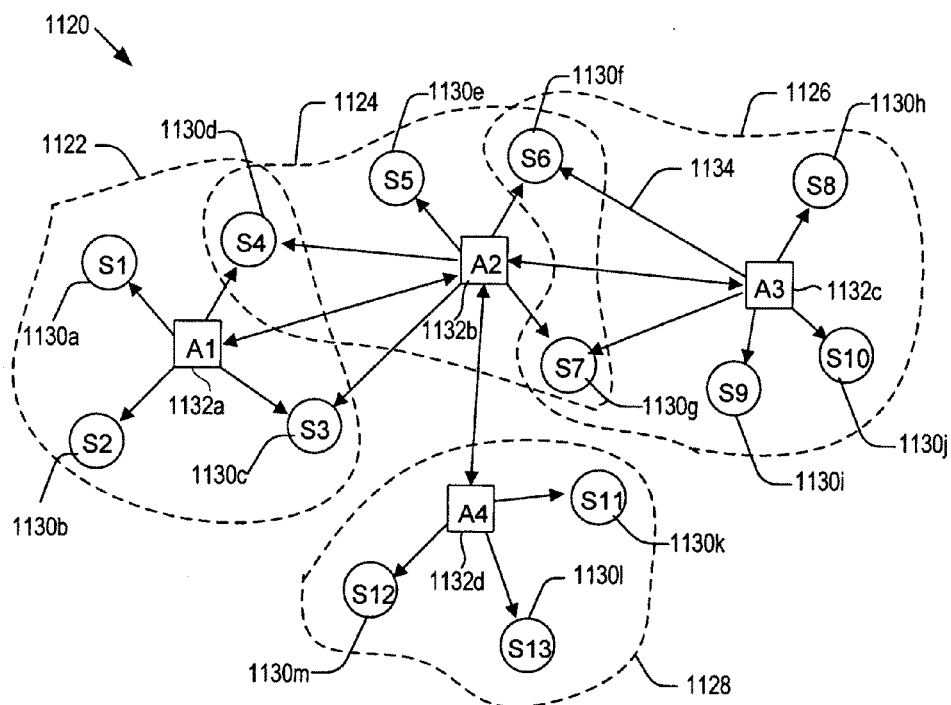
FIG. 11B is a schematic diagram of a network architecture having actuators/sensors subgroups in accordance with another embodiment of the present invention.

FIG. 11B illustrates another example of actuator/sensor network architecture 1120 that may include subgroups partitioned by the interrogation module in accordance with another embodiment of the present invention. As illustrated in FIG. 11B, four subgroups 1122, 1124, 1126 and 1128 may be generated using four actuator/sensors 1132a-1132d and thirteen sensors 1130a-1130m. Table 2 shows the elements of each subgroup formed of the patches in FIG. 11B.

TABLE 2

Subgroups made of seventeen patches in FIG. 11B

| Subgroup number | actuator | sensors |
| --- | --- | --- |
| 5 | A1 | A2, S1, S2, S3, S4 |
| 6 | A2 | A1, A4, S3, S4, S5, S6, S7 |
| 7 | A3 | A2, S6, S7, S8, S9, S10 |
| 8 | A4 | A2, S11, S12, S13 |

It is noted that each of the thirteen sensors 1130a-1130m in FIG. 11B may also function as an actuator. However, only one patch in each subgroup will operate as an actuator at one point in time while the other patches are synchronized to operate as sensors. As in the case of FIG. 11B, one sensor (such as s3) may belong to more than one subgroup (group 5 and 6). In FIGS. 11A-B, only four actuator/sensors and thirteen sensors are shown for clarity illustration. However, it should be apparent to those of ordinary skill that the present invention may be practiced with any number of patches.

The network architecture of a diagnostic patch system, such as shown in FIGS. 11A-B, can be configured to maximize overall network performance with the minimum number of the actuators and sensors. The diagnostic network can be represented by an undirected graph G=(N,E), in which the nodes N and edges E represent the patch sites and wave-communication paths, respectively. The graph G may be a picture of the relation of the diagnostic network communication, whereas the node points 1102, 1104, 1006, 1108 in FIG. 11A represent the elements of actuator and sensor sets, and solid lines as edges 1110 in FIG. 11A represent the ordered pairs in the relation from the actuator set and the sensor set in the Table 1. A graph G is connected if there is at least one path between every pair of nodes i and j. In an exemplary optimal design for network path uniformity, the following notation may be defined: n is the number of nodes; $x_{ij} \in \{0,1\}$ is a decision variable representing paths between nodes i and j; and $x(=\{x_{12}, x_{13}, \ldots, x_{n-1,n}\})$ is a topological architecture of network design. R(x) is a constraint of network design, such as the number of the patches; $c_{ij}$ is the cost variable of the network design, such as the distance of Lamb wave propagation, the number of intersection points on each network path being crossed by other network paths or the sensitivity factor to excitation frequency. The optimal design of diagnostic network can be represented as follows:

$$arg\ max\ Z(x) = \sum_{i=1}^{n-1} \sum_{j=i+1}^{n} c_{ij} x_{ij}\ s.t.\ R(x) \geq R_{min},$$

where this optimal problem must be solved for the values of the variables $x(=\{x_{12}, x_{13}, \ldots, x_{n-1,n}\})$ that satisfy the restriction $R_{min}$ and meanwhile minimize the objective function Z(x) representing network path uniformity.

In another example of optimal group design, each of the sensors in a network subgroup may be associated with one actuator of the group as illustrated in FIG. 11B. The network performance may depend on the position and the number of the actuator and sensors in each subgroup. For this group layout of patches, an actuator/sensor matrix may be considered, where each element (i,k) of the matrix is 1 if the $i^{th}$ sensor is associated by the $k^{th}$ actuator and 0 otherwise. In such a group design, a common integer programming formulation, which consists of the following assignment of variable declarations and constraint, may be applied. Each actuator may be assigned to only one subgroup, where each sensor may assigned to more than one subgroup: $x_{ic}$ is 1 if $i^{th}$ actuator is assigned to subgroup c and 0 otherwise; $y_{ic}$ is 1 if $j^{th}$ sensor is assigned to subgroup c and 0 otherwise. Two constraints may be expressed as:

$$\sum_{c=1}^{k} x_{ic} = 1, i = 1, \ldots, m\ \text{and}\ \sum_{c=1}^{k} y_{jc} = 1, i = 1, \ldots, n,$$

where k is the number of subgroups specified, and m, n are the number of actuators and sensors, respectively.

Referring back to FIG. 10, a genetic algorithm implemented in the interrogation module may design the network and signal paths in step 1004. One or more artificial defects, such as small detachable patches, may be applied to the host structure to simulate damages. Then, each actuator may send signal to sensors in one or more of the partitioned subgroups. Based on the signals received by the sensors, the genetic algorithm may determine the optimum network, signal paths and sequence order of the actuators so that the locations and types of the artificial defects can be accurately detected. Depending on the geometrical shapes and materials of the host structure, the determination of subgroup sets may include the step of adjusting the number of actuator/sensors in the communication network.

In step 1006, the actuator in $i^{th}$ subgroup may be activated to generate the Lamb wave signals according to the sequential order from the relay switch array module 512 (shown in FIG. 5A). Then, the signals carrying structural condition information (SCI) may be measured by the sensors of $j^{th}$ subgroup in step 1008, where the $j^{th}$ subgroup may include the $i^{th}$ subgroup. In step 1010, the interrogation module may compute the deviation of the measured signals from baseline signals, wherein the baseline signals may be prepared by performing the steps 1004 and 1006 in the absence of the artificial defects. Next, the interrogation module may store the deviation and measured signals into a suitable signal database depository (such as computer 514) as eXtensible Markup Language (XML) formatted documents in step 1012. In addition, the interrogation module may save the coordinates of the actuators and sensors as well as the set-up information data including the actuation frequency, the identification number of the actuators and sensors, voltage level, patch type and operational failure status. Subsequently, the interrogation module may stop the interrogation process in step 1014.

Figure 12:
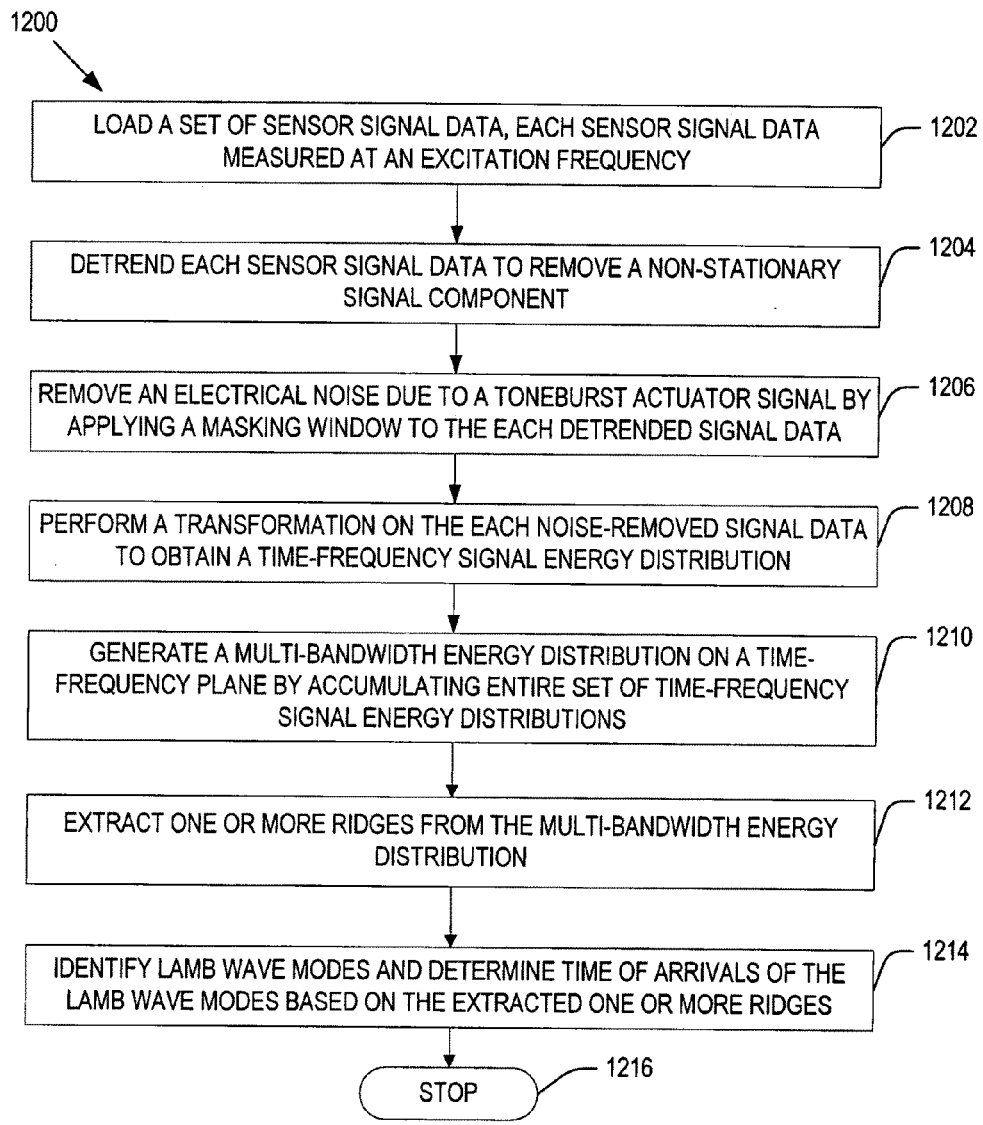
FIG. 12 is a flow chart illustrating exemplary procedures for identifying Lamb wave modes in accordance with one embodiment of the present invention.

The interrogation module may perform the steps 1006, 1008, 1010 and 1012 at discrete set of excitation frequencies, where the actuators of the DNP system may be activated at each excitation frequency to generate Lamb waves. Then, the process module may process the stored sensor signals to determine structural condition index (SCI) for each network path at an excitation frequency. The SCI of a network path between a pair of actuator and sensor refers to a quantity that may be affected by damages of the host structure and, as a consequence, represent the degree of structural condition changes probably located in the interior region of the host structure. The SCI may include, but not limited to, the time-of-arrivals for Lamb wave modes, the spectrum energy for Lamb wave modes distributed on their time-frequency domain or peak amplitude of sensor signal. FIG. 12 is a flow chart illustrating exemplary procedures 1200 for identifying and determining the time-of-arrivals for Lamb wave modes in accordance with one embodiment of the present invention. In step 1202, the process module may load a set of sensor signal data from a signal database depository, such as computer 514, where each sensor signal data may be measured at one excitation frequency. Hereinafter, the excitation frequency refers to a frequency at which the actuators of the DNP system are activated to generate Lamb waves. The stored set-up information data for the network patch system may be checked and the network path numbers may be identified to check whether the appropriate actuator and sensor are assigned to the path of each network link. Then, in step 1204, the process module may detrend each of the loaded sensor signal data to remove a non-stationary signal component. Next, in step 1206, the electrical noise 914 due to the toneburst actuator signal 904 may be removed by applying a masking window 918 to the detrended each signal data. Subsequently, in step 1208, the short-time Fourier or wavelet transformation may be performed on the noise-removed signal data to obtain a time-frequency signal energy distribution about the center frequency bandwidth of excitation along the time axis.

In step 1210, the process module may perform accumulating entire set of time-frequency signal energy distributions to generate a multi-bandwidth energy distribution on the time-frequency plane. Then, in step 1212, the process module may extract ridges (curves) from the multi-bandwidth energy distribution on the time-frequency plane. The ridges extracted from this energy distribution can show the trajectory curve of each wave mode and provide the local maxima along the frequency axis. In the ridge extraction, searching the local maxima may be done on a fixed value in time axis where the maximum in the row of the distribution data may be compared to new two rows given by shifting the row one-step in both directions and this maximum may be stored if it is greater than a predefined threshold. In step 1214, based on the ridge curves, the process module may identify the trajectory of the $S_0$, $S_{0\_ref}$ and $A_0$ mode waves (926, 928 and 930 of FIG. 9) on the time-frequency plane. Then, the process module may stop identifying process in step 1216.

As will be explained later, the trajectory of the $S_0$, $S_{0\_ref}$ and $A_0$ mode waves determined in step 1214 may be utilized for designing the moving envelope windows of various time spans with respect to the mode waves. The ridge extraction method may provide an accurate determination of the arrival time of each mode wave so that the phase velocities and the arrival-time differences between these modes can be exactly computed instead of calling for a dispersion curve formula of the structure. It is noted that the scope of the invention is not limited to the use of wavelet transformation in the time-frequency interpretation method.

Figure 13A:
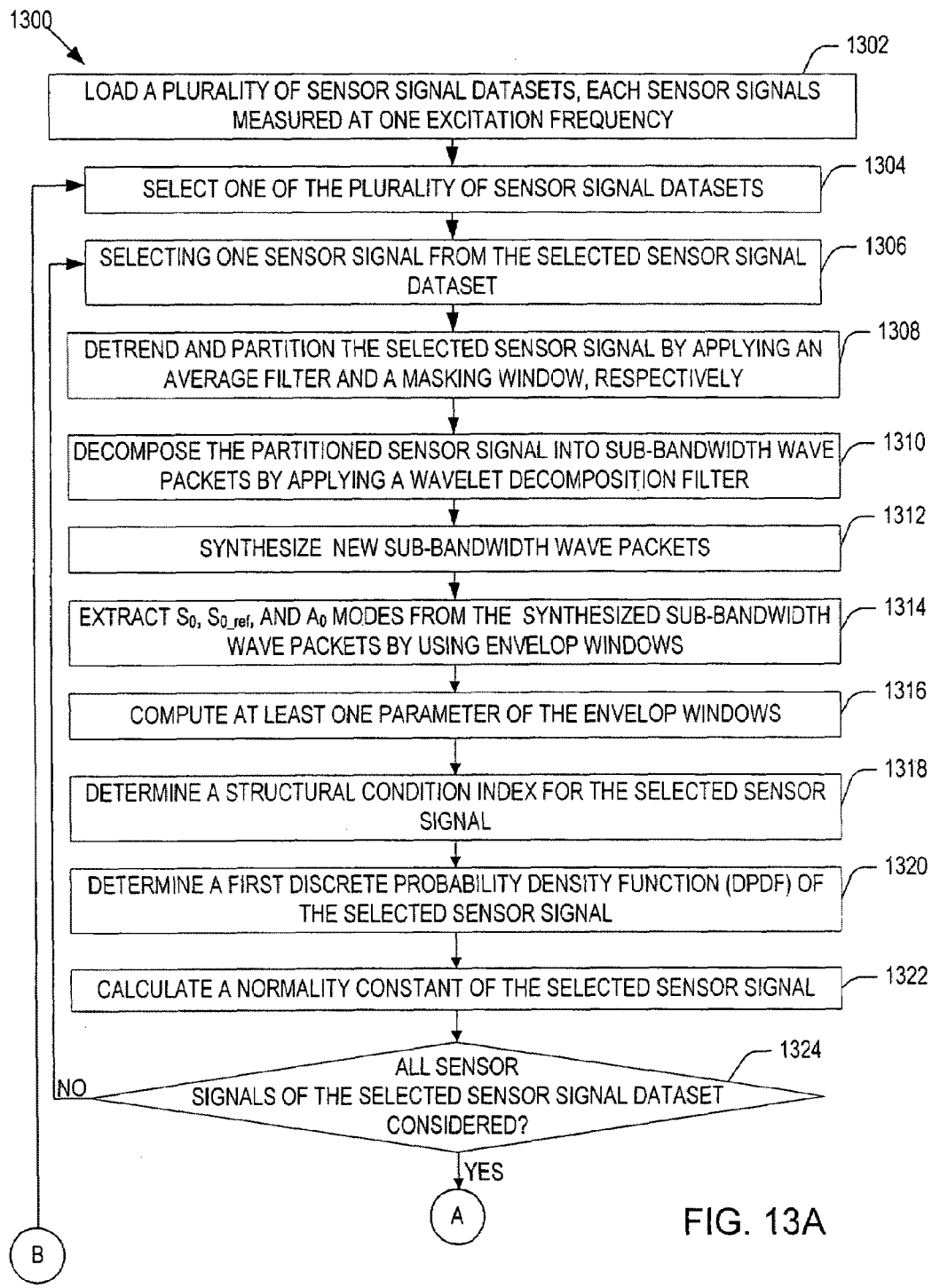
FIGS. 13A-B show a flow chart illustrating exemplary procedures for computing SCI values in accordance with one embodiment of the present invention.
Figure 13B:
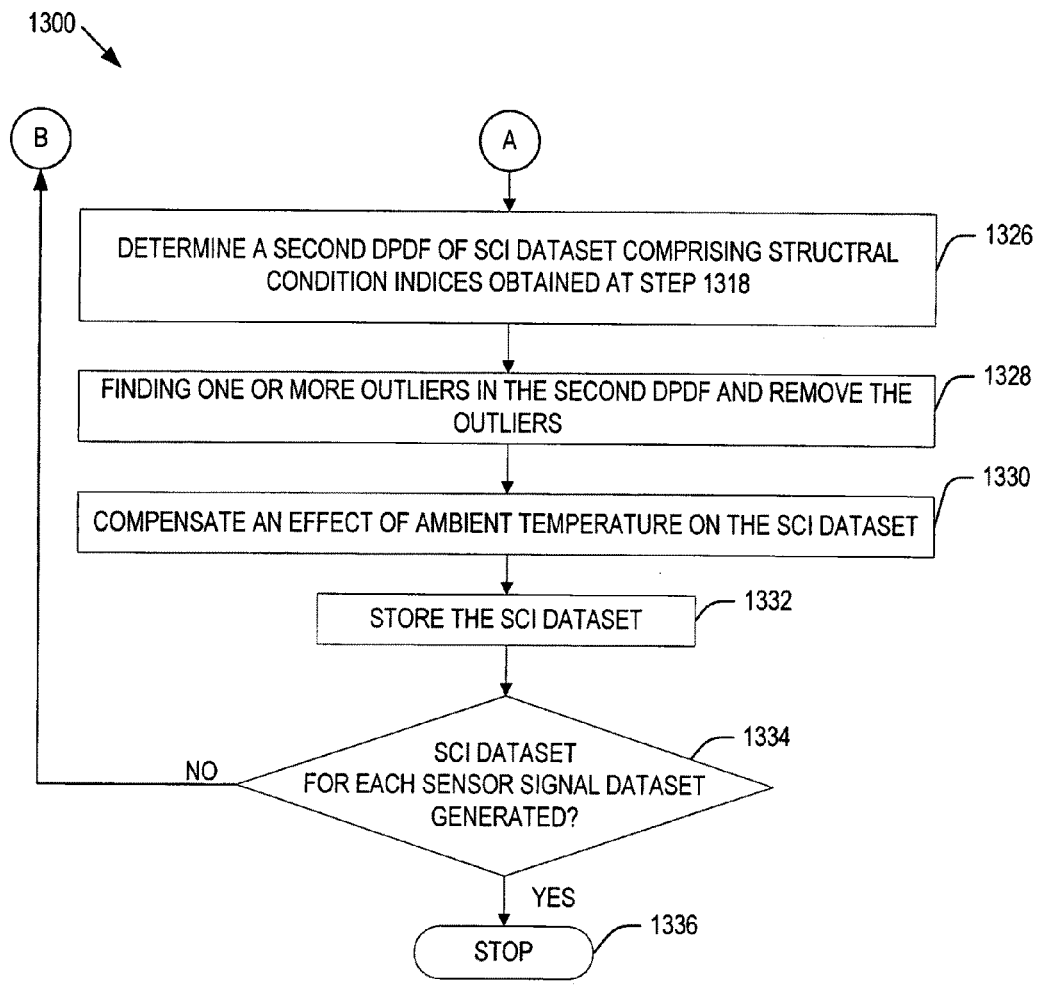

FIGS. 13A-B show a flow chart 1300 illustrating exemplary procedures for computing SCI values (or, equivalently, damage index values) in accordance with one embodiment of the present invention. To compute SCI values, the process module may use the sensor signal dataset measured at a set of excitation frequencies. In step 1302, the process module may load a plurality of sensor signal datasets, where each sensor signal dataset is measured at one excitation frequency, where each sensor signal of a dataset, such as the signal 912, may correspond to a network path of the DNP system. Then, in step 1304, one of the plurality of sensor signal datasets may be selected. Subsequently, a sensor signal may be selected from the selected sensor signal data set in step 1306. In step 1308, the selected sensor signal may be detrended by applying a moving-average filter and partitioned into the actuation part 914 and receiving part 916 by applying a masking window 918 (shown in FIG. 9). In step 1310, the sensor signal may be decomposed into the several sub-bandwidth wave packets 926, 928 and 930 by a wavelet decomposition filter that preferably uses the Daubechies wavelet filter coefficients. For sub-bandwidth wave packet decomposition, a dyadic filter is designed for the Daubechies wavelet filter coefficients to provide high and low decomposition, and high and low reconstruction filter. The decomposition filter decomposes the detrended signal into the wavelet coefficients for multiresolution levels. Next, in step 1312, the process module may synthesize new sub-bandwidth wave packets within the frequency range of interest, where the Lamb wave signal may contain the waves of $S_0$, $S_{0\_ref}$ and $A_0$ modes in the frequency bandwidth. The frequency range in a synthesized signal may be determined using a ridge extraction method to cover the range of the sub-bandwidth variation of each wave signal such that the multi resolution levels selected in the reconstruction filter may correspond to the bandwidth of the synthesized signal containing the wave signals of $S_0$, $S_{0\_ref}$ and $A_0$. The synthesized signal is then generated using the reconstruction filer and the wavelet coefficients in signal decomposition. Then, in step 1314, the process module may apply signal extracting windows (or equivalently, moving envelop windows) 920, 922 and 924 to the synthesized Lamb wave signal to extract the $S_0$, $S_{0\_ref}$ and $A_0$ mode waves 926, 928 and 930 as independent waveforms. Each of $S_0$, $S_{0\_ref}$ and $A_0$ mode waves 926, 928 and 930 may be fitted within an envelop of each wave mode. In step 1316, the process module may determine the maximum, center position and span width of each of the envelope windows 920, 922 and 924 in the time axis. Then, it may compute in step 1318 SCI for the selected sensor signal. In one embodiment, the SCI may be based on the change in the spectrum energy of each wave of the $S_0$, $S_{0\_ref}$ and $A_0$ modes. In this embodiment, the process module may determine the spectrum energy of each wave of the $S_0$, $S_{0\_ref}$ and $A_0$ modes. Next, the process module may calculate the summation of these spectrum energies of the $S_0$, $S_{0\_ref}$ and $A_0$ modes and determine the difference in the summed energies between the baseline and damaged conditions of the host structure. Consequently, the spectrum energy difference may be utilized as a SCI value of the selected sensor signal. In an alternative embodiment, the process module may choose the changes in the maximum and center positions of the envelope windows as the SCI values.

Moreover, if the diagnostic measurement system use traditional vibration sensors such as accelerometers, displacement transducers or strain gauges, the process module can compute structural dynamic parameters, such as natural frequencies, damping ratios or mode shapes, from vibrational signal dataset obtained at a plurality of vibration sensor locations. The process module may exploit the change in structural dynamic parameters as the SCI values when traditional vibration sensor signals are used instead of Lamb wave signals, as another alternative embodiment.

After the process module computes the SCI data for all the network paths, it may remove abnormal sensor signals possibly included in two datasets of the sensor signals corresponding to the baseline and damaged conditions of the host structure. For this purpose, the process module may evaluate whether each sensor signal may have reasonable distribution of signal amplitudes in terms of probability. In step 1320, the process steps may determine the discrete probability density function (DPDF) on the signal amplitudes, and estimate the 2nd, 3rd and 4th moments of $$1/N \sum_{i=1}^{N} x_i^{2,3,4} p(x_i)$$

for the amplitude distribution $p(x_i)$. From these estimates of the amplitude distribution, the covariance $\delta$, skewness factor $\eta$, and flatness factor $\kappa$ of the DPDF may be used to determine, in step 1322, a normality constant $\alpha$ on each sensor signal. The normality factor may be defined in terms of the product of these factors with power weightings: $\alpha=\delta^{3/2}\eta^{-2}\kappa^{3/4}$. In step 1324, the process module may check if all of the sensor signals contained in the selected sensor signal dataset have been considered. Upon negative answer to the decision step 1324, the process may proceed to the step 1306. Otherwise, the process may proceed to step 1326 in FIG. 13B.

In step 1326, the process module may compute the second PDF of a SCI dataset comprising SCI values for the sensor signals contained in the selected sensor signal dataset. Then, based on the second PDF, it may find the outliers of SCI values outside the 3-sigma of the SCI distribution in step 1328. By checking the normality constants of the SCI outliers, the process module may delete the SCI values of the outliers from the SCI dataset for more reliable structural health monitoring.

As the change in ambient temperature during the measurements of sensor signals can influence the sensor signals of Lamb waves, the SCI values obtained from the Lamb wave sensor signals should be modified to compensate for the difference in ambient temperatures between the baseline and damaged structure conditions. The process module may check whether the measurement temperature of the baseline is different from that of the damaged structure condition. The process module may prepare a temperature reference table of Lamb waves. To establish the reference table, it may compute the time-span widths and maxima of the $S_0$-mode envelopes for all of the network paths of the baseline structure and determine the average of the time-span width data for the 95% network paths in the envelope maximum distribution. With the help of the reference table, the process module can calculate a temperature-adjustment parameter as the average ratio of the time-span-width in the baseline structure signals to the reference table value corresponding to the temperature of the damaged structure. In step 1330, the process module may compensate the effect of ambient temperature change on the sensor signals by scaling the SCI data of the damaged structure with the temperature-adjustment parameter. Next, the process module may store the SCI dataset as eXtensible Markup Language (XML) formatted documents in step 1332. Subsequently, in a determination step 1334, the process module may check if the SCI dataset for each of the excitation frequencies have been generated. Upon negative answer to the decision step 1334, the process may proceed to the step 1304. Otherwise, the process module may stop the process in step 1336.

Figure 14A:
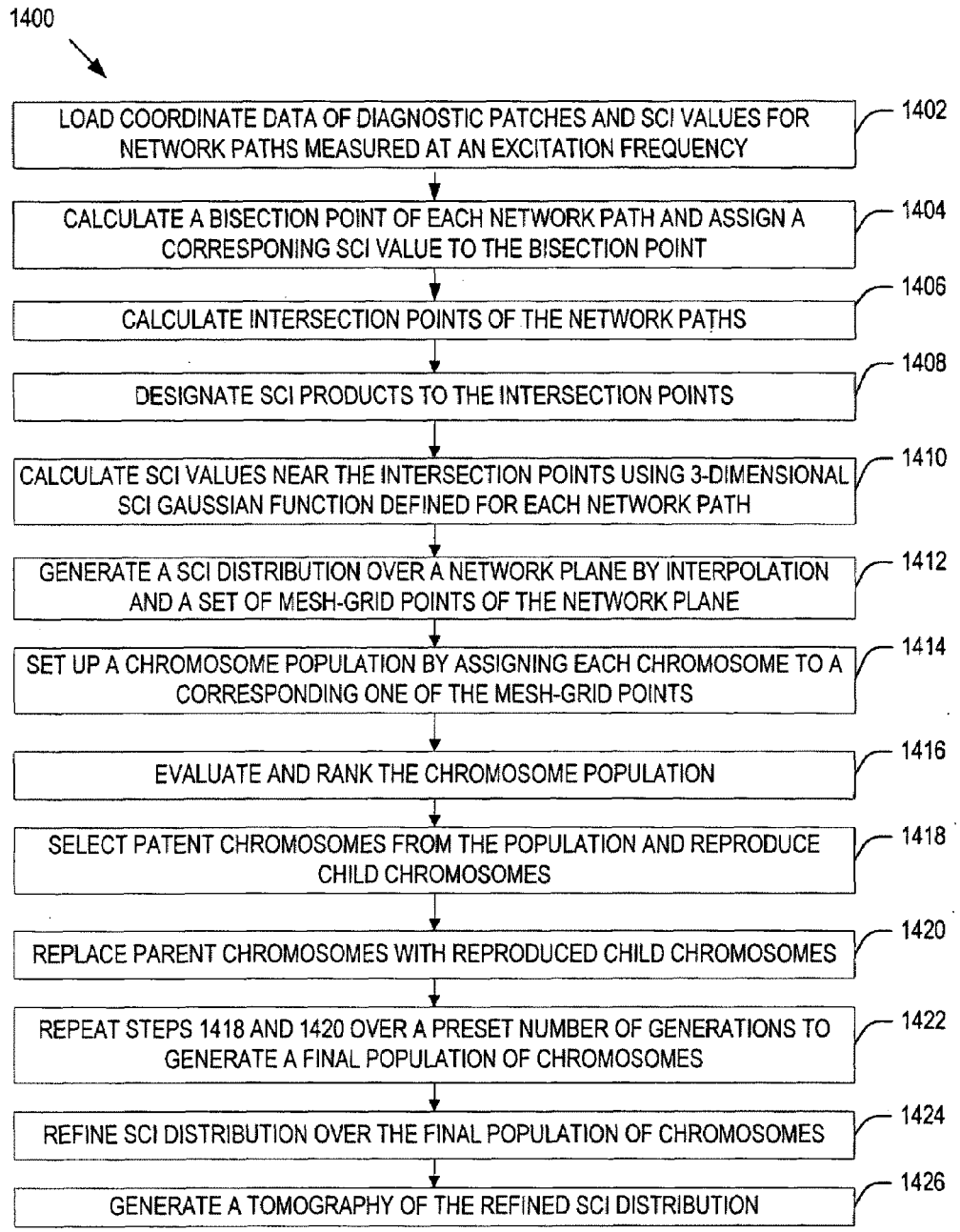
FIG. 14A is a flow chart illustrating exemplary procedures for generating a tomographic image to identify the regions having changes in structural conditions or damages in accordance with one embodiment of the present invention.

FIG. 14A shows a flow chart 1400 illustrating exemplary procedures for generating a tomographic image to identify the regions having changes in structural conditions or damages in accordance with one embodiment of the present invention. In step 1402, the process module may load the coordinate data for diagnostic patches and SCI values for the network paths defined by the diagnostic patches. For any $i^{th}$ network path line, the bisection point of a network path may be calculated in step 1404 from the actuator and sensor coordinates of $\{x_i^{act}, y_i^{act}\}$ and $\{x_i^{sen}, y_i^{sen}\}$ as the half of the minimum distance of the path line, tangential to the surface of the structural geometry. Then, the SCI value of the $i^{th}$ network path may be designated to the bisection point of the $i^{th}$ network path. Next, the process module may calculate intersection points of the network paths in step 1406. The process module may calculate the slope of $m_i=(y_i^{sen}-y_i^{act})/(x_i^{sen}-x_i^{act})$, its inverse $\overline{m}_i=1/m_i$, and the constants of $C_i=y_i^{act}-m_ix_i^{act}$ and $\overline{C}_i=x_i^{act}-\overline{m}_iy_i^{act}$ for the $i^{th}$ path line. Then, the process module may determine the coordinate $\{(C_k-C_i)/(m_i-m_k), (m_iC_k-m_kC_i)/(m_i-m_k)\}$ on the $i^{th}$ path line for all of the other $k^{th}$ path lines intersecting the $i^{th}$ path line, with the condition on the slope $m_i$ to meet $(C_k+m_kx_k^{sen}+y_k^{sen})/(\overline{C}_k+\overline{m}_ky_k^{sen}-x_k^{sen}) \leq m_i \leq (\overline{C}_k+m_kx_k^{act}-y_k^{act})/(C_k+\overline{m}_ky_k^{act}-x_k^{act})$. In step 1408, the process module may calculate the product of SCI values of the $i^{th}$ and $k^{th}$ network paths to assign a new SCI on each of the intersection points. In the case of no intersection, the designated SCI may be the half of the SCI value of the $j^{th}$ path line and the intersection point may be the same as the bisection point. Thus, the SCI values considered as the z-axis data on the coordinate plane of the actuators and sensors in the network path lines may be assigned to all of the bisection and intersection points. In one embodiment, the SCI data of all the bisection and intersection points may be stored as eXtensible Markup Language (XML) formatted documents into a SCI database depository.

For any $i^{th}$ path line, the process module may set a z-axis Gaussian or generalized bell function in the plane normal to the path line direction such that the maximum at the center of the Gaussian function may be the SCI value of the path. In step 1410, this z-axis function may be used to create a 3-dimensional block on the network path coordinate plane, in the manner that the cross section of the Gaussian function may run in parallel to the path line from the beginning and the end of the path line. Actually, this 3-dimensional function of the $i^{th}$ path line may intersect by being overlapped with other 3-dimensional functions of any other $k^{th}$ path lines. The SCI values at the intersection area may be determined by the product of the intersecting Gaussian SCI functions on the network path coordinate plane. The width of this 3-dimensional function in the cross-section plane may be the shortest distance in all the path lines, which is multiplied by the SCI value ratio of the $i^{th}$ path to the shortest distance path line. The process module may continue to compute the SCI values on the network plane until all the network paths are considered. In step 1412, the process module may interpolate the SCI dataset for each of the bisection, the intersection and the 3-dim Gaussian-function overlapping points over the meshgrid points, made by dividing the entire region of the structure into small mesh elements. In this interpolation, the process module may employ the Delaunay triangulation of the convex-hull set for the grid data of SCI values.

By applying a genetic algorithm, the process module may further refine the SCI distribution on the network path plane to precisely locate the damaged regions in the host structure. In step 1414, the process module may setup an initial population of chromosome and assign each chromosome to a corresponding one of the mesh-grid points. Then, in step 1416, the process module may rank the chromosomes by evaluating them with the correlation of the SCI distribution data of the neighboring grid points. In step 1418, the process module may select parents from the population using a random-selection procedure biased so that the parents with highest evaluations are most likely to reproduce. The process module may also reproduce children from some combination of the parents so that possible random mutation of children takes place. Then, in step 1420, the parent chromosomes may be replaced by the children chromosomes. Steps 1416-1420 may be repeated over a number of generations until a complete new population of children is established in step 1422, where the children may be evaluated and the entire population of parents is replaced to become parents themselves. Then, in step 1424, the process module may get the refined SCI distribution on the gird points with the composition of the final population of chromosomes.

The SCI distribution on the mesh-grid points corresponding to the final chromosomes may represent the degree of changes in the structural condition of the host structure. The regions of area where the structural condition changes or damages may occur in the host structure can be exactly identified from this refined SCI distribution. In step 1426, for the structural condition or damage identification of the host structure, the process module can provide a genetic-based tomography image using the interpolated SCI distribution. Also, by repeating the steps 1402-1426 at a set of excitation frequencies, a set of tomographic images may be obtained.

Figure 14B:
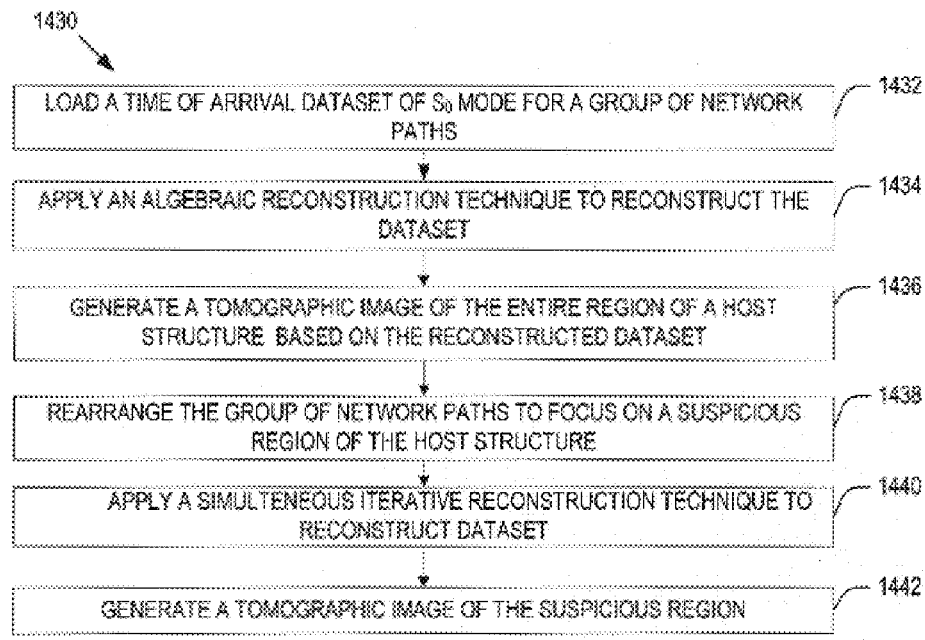
FIG. 14B is a flow chart illustrating exemplary procedures for generating a tomographic image to identify the regions having changes in structural conditions or damages in accordance with another embodiment of the present invention.

FIG. 14B is a flow chart 1430 illustrating exemplary procedures for generating a tomographic image to identify regions having changes in structural conditions or damages in accordance with another embodiment of the present invention. In step 1432, the process module may load a time-of-arrival dataset of a Lamb wave mode, such as $S_o$ mode. As mentioned, the time-of-arrival for a Lamb wave mode can be used as a SCI. Using the extracted ridge curves in step 1212, the process module may exactly determine for all the network paths the time-of-arrival differences between the Lamb wave modes. Next, in step 1434, a conventional algebraic reconstruction technique may be applied to the loaded time-of-arrival dataset for the global inspection of damage on the host structure. Then, based on the reconstructed time-of-arrival data, a tomography of the entire region of the host structure may be generated in step 1436. In one embodiment, the steps 1432-1436 may be repeated to generate a set of tomographic images of the entire region, where each tomographic image may be based on a time-of-arrival dataset measured at a different excitation frequency. By stacking the set of tomographic images, a hyperspectral tomography cube of the entire region may be obtained.

The process module can also employ a simultaneous iterative reconstruction technique to investigate the defect characteristics of a suspicious region of the host structure. In step 1438, the network paths may be rearranged to focus on a suspicious region. Then, in step 1440, the process module may apply the simultaneous iterative reconstruction technique to the loaded time-of-arrival dataset to investigate the defect characteristics of the suspicious region. Next, based on the reconstructed dataset, a tomographic image of the suspicious region may be generated in step 1442. In one embodiment, the steps 1432-1442 may be repeated to generate a set of tomographic images for the suspicious region, where each tomographic image may be based on a time-of-arrival dataset measured at a different excitation frequency. By stacking the set of tomographic images, a hyperspectral tomography cube of the suspicious region may be obtained.

In another embodiment, the genetic-based distribution on the time-of-arrival dataset of the network paths, incorporated with the ridge extraction method for the short-time-Fourier-transformation (STFT) of sensor signals, may be also used to determine the SCI distribution and generate a tomographic image. In this embodiment, the tomographic image may be different from those in the steps 1436 or 1442. The method of the ridge extraction and genetic-based distribution for Lamb-wave time-of-arrival dataset can employ the scattering-operator-eigenfunction based tomography-imaging techniques known in the art.

Figure 14C:
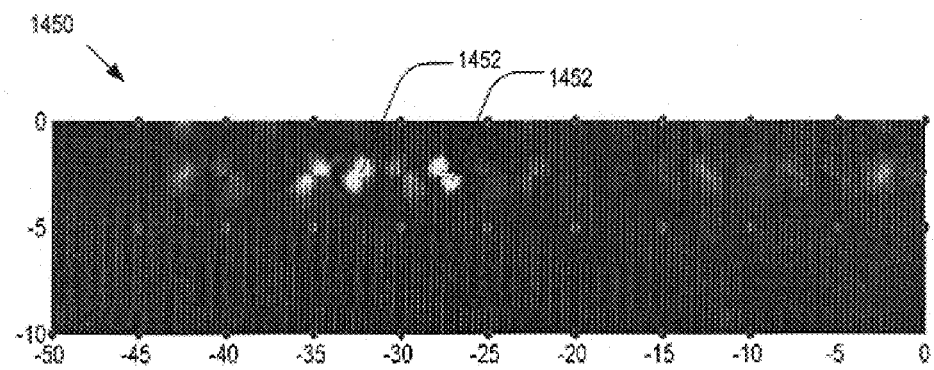
FIG. 14C is a tomography image generated by the procedures of FIG. 14A.

When the process module displays a color tomographic image, the range of colors may be adjusted to enhance the visibility of the 'hot-spot' zones having damage with respect to the background color. In addition, the tomographic image can have colored marks and dotted lines to show the locations of actuators and sensors and the network path lines over a 2 or 3-dimensional image of the structural geometry. The process module may store the tomographic images as well as the range of colors into a tomography database depository. FIG. 14C shows an example of tomography image 1450 obtained in step 1426, where the image is expressed in a gray scale. As can be noticed, the regions 1452 may represent damages.

Figure 14D:
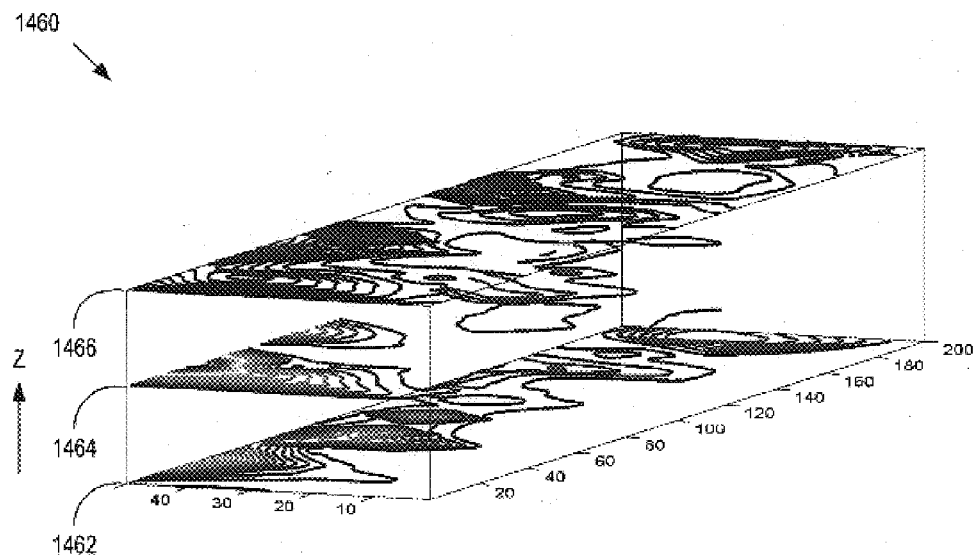
FIG. 14D shows a hyperspectral tomography cube in accordance with one embodiment of the present invention.

FIG. 14D shows a hyperspectral tomography cube 1460 in accordance with one embodiment of the present invention. As illustrates in FIG. 14D, the hyper spectral tomography cube 1460 comprises layers of two-dimensional tomographic images 1462, 1464 and 1466, where each image may be generated at an excitation frequency and the z-axis may represent the excitation frequency. For simplicity, only three layers 1462, 1464 and 1466 are shown in FIG. 14D. However, it should be apparent to those of ordinary skill that the hyperspectral tomography cube 1460 may comprise image layers generated at continuous excitation frequency range.

Figure 14E:
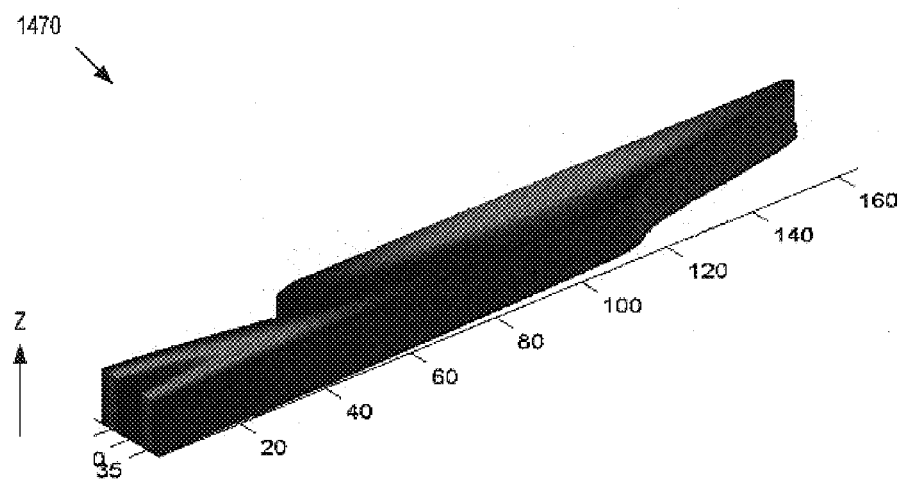
FIG. 14E shows a 3-dimensional damage evolution manifold illustrating the variation of structural condition in accordance with one embodiment of the present invention.

FIG. 14E shows a 3-dimensional damage evolution manifold 1470 illustrating the variation of structural condition in accordance with one embodiment of the present invention. Like the hyperspectral tomography cube 1460, the manifold 1470 may comprise two-dimensional tomographic images stacked in z-direction, wherein each image is generated after a number of vibrational repetition cycles corresponding to the z-value has been applied to the host structure. Also, in each tomographic image, only a portion that shows structural changes has been displayed. Thus, each of slices on the 3-dim damage-evolution manifold 1470 may represent the evolution state of structural condition or damage in a structure.

Figure 15A:
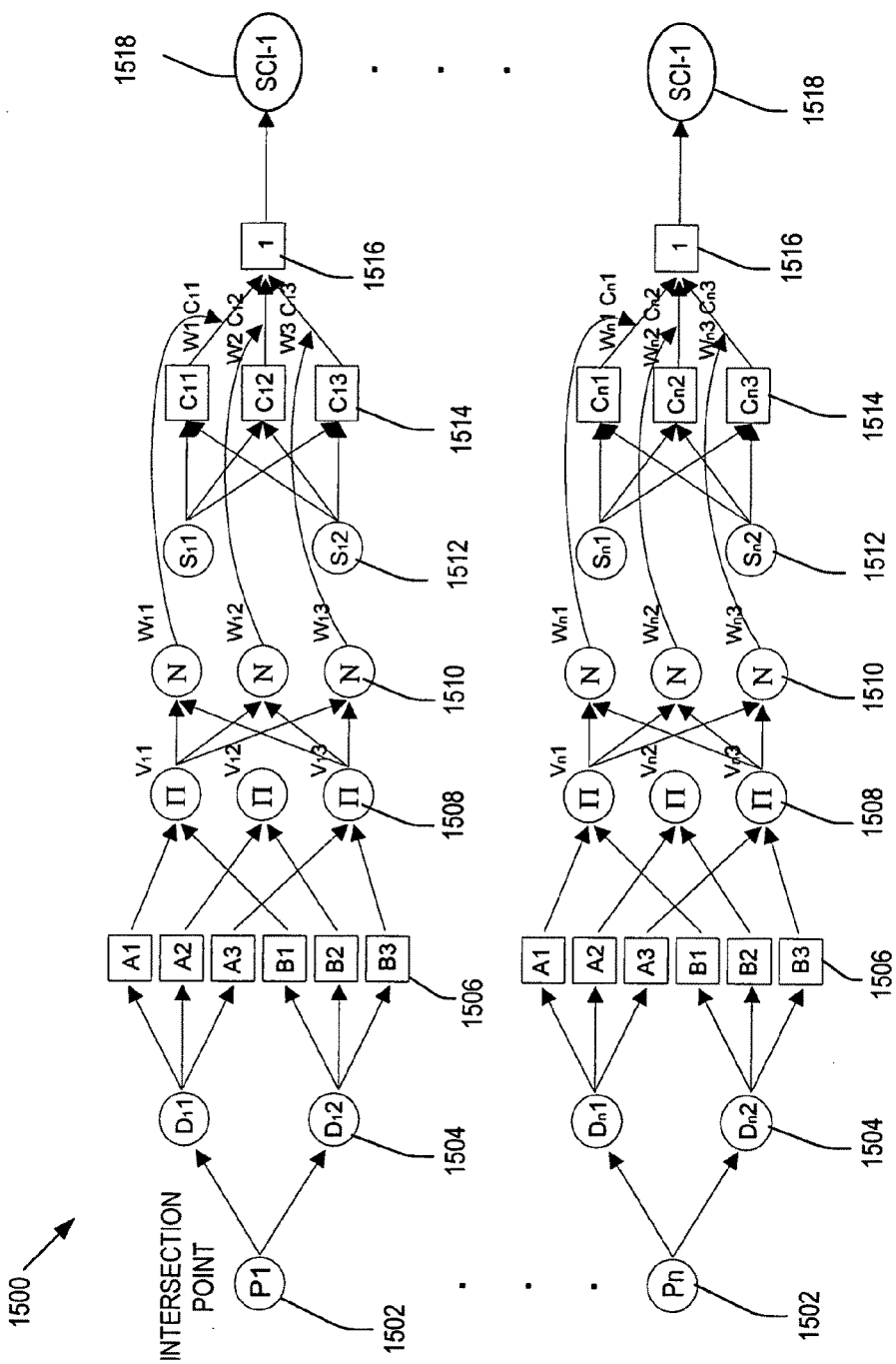
FIG. 15A is a schematic diagram illustrating exemplary procedures of a neuro-fuzzy inference system for providing structured system condition index (SCI) distribution at the intersection points of network paths in accordance with one embodiment of the present invention.

As mentioned in the step 1410 of FIG. 14A, the process module may determine SCI values near the intersection points of network paths. A classification module that includes a neuro-fuzzy inference system may also determine the SCI values at the intersection points. FIG. 15 is a schematic diagram 1500 illustrating procedures of a neuro-fuzzy inference system for providing structured system condition index (SCI) distribution at the intersection points of network paths in accordance with one embodiment of the present invention. As explained in step 1408, each of the intersection points in the network paths has two crossing path lines with their SCI values and distances. To obtain structured SCI values at the intersection points, the distance of two crossing path lines may be exploited by a fuzzy if-then rule system collaborated with a neural network. Then, this expert system may generate the output of SCI values of the intersecting paths.

For any of the n intersection points P1-Pn 1502, each of two crossing path line distances 1504 can be input into three fuzzy membership functions 1506, ($A_1/B_1$, $A_2/B_2$, $A_3/B_3$), in the terms of "short", "medium", "long" distance. For the membership function, generalized bell functions of $\mu_{A_i/B_i}=1/[1+|(x-c_i)/a_i|^{2b}]$, i=1, 2, 3, may be used with the adjustment parameters of (a, c) to cover each input region of the path line distance normalized to a structure dimension. In layer 1508, every node may be a fixed node labeled Π and generate an output $v_i^k$ that may be the product of the incoming signals of $A_i, B_i: v_i^k = \mu_{A_i}(x^k)\mu_{B_i}(x^k)$, k=1, . . . , n. Each node output may represent the firing strength of a rule. Any $i^{th}$ node of layer 1510, labeled N, may calculate the ratio $w_i^k$ of the $i^{th}$ rule's firing strength to the sum of all rules' firing strengths: $w_i^k = v_i^k/(v_1^k + v_2^k + v_3^k)$, i=1, 2, 3 so that the output $w_i^k$ of the layer 1510 may be a normalized firing strength. Moreover, SCI values of step 1408 at intersecting paths in layer 1512 may be inputted into a multilayer perception or neural network. In layer 1514, each node may be adapted with a node function of, $c_i^k = f_i^k(s_1^k, s_2^k)$, i=1, 2, 3 where $c_i^k$ is the consequent parts in a network-layered representation which can be compared with a simple backpropagation multilayer perception with the input layer 1512 of SCI values $s_i^k$, Here, $f_i^k(s_1^k, s_2^k)$ require two SCI values of the intersecting path lines as input. If all three neurons 1514 and one neuron 1516 have identity functions in FIG. 15A, the presented neuro-fuzzy is equivalent to Sugeno (TSK) fuzzy inference system, which accomplishes linear fuzzy if-then rules. Adjusting the relevant connection strengths or weighting factors on the neural network link according to the error distance may initiate the adaptation in the neural network. In one embodiment, a sigmoidal function may be used as the neuron function in the consequent layer 1514. In another embodiment, the neural network layer can use a back propagation multilayer perception and radial basis function networks. In layer 1516 as an output of the consequent layer 1514, the node may compute the summation of all incoming signals like $y_k = \Sigma_i w_i^k c_i^k / \Sigma_i w_i^k$ and generate output 1518 that may comprise the SCI values at intersection points.

Figure 15B:
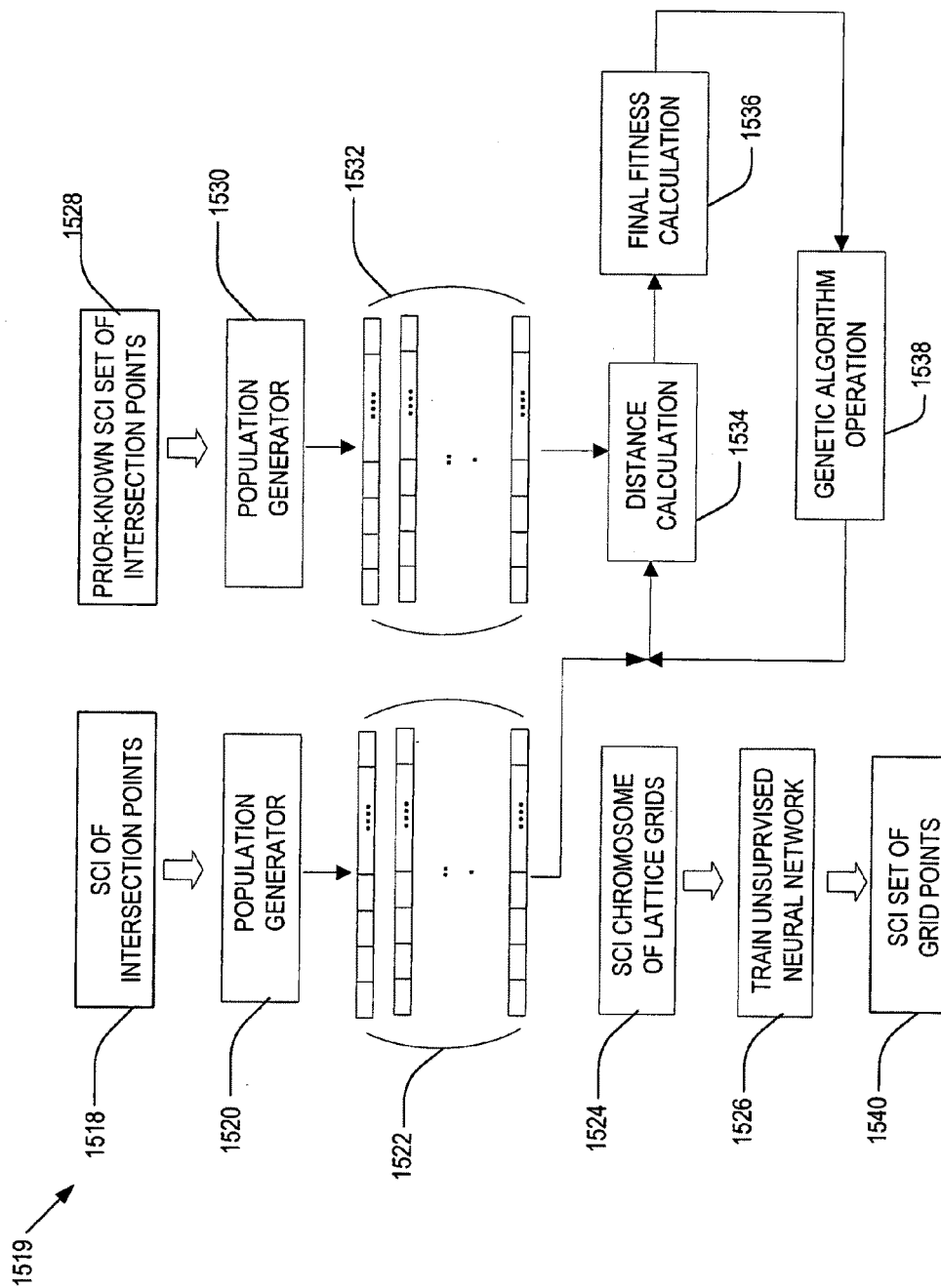
FIG. 15B is a schematic diagram illustrating exemplary procedures of a cooperative hybrid expert system for simulating SCI distribution on the lattice grid points of a structure in accordance with one embodiment of the present invention.

FIG. 15B is a schematic diagram 1519 illustrating exemplary procedures of a cooperative hybrid expert system for simulating SCI distribution on the mesh-grid (or, equivalently, lattice grid) points of a structure from SCI distribution on the intersection points in accordance with one embodiment of the present invention. For artificial damage such as attachment of the various-sized rubber patches on a structure with the prior-known information on the location and extent of the damage, the classification module can generate output 1528 that may be the first SCI chromosomes $s_{prior}^j$ the grid points following the steps 1418-1426. If the input 1518 to this corporative hybrid expert system is the SCI distribution on the intersection points given with the coordinates of the rubber patches and their sizes, the final output 1540 of this cooperative hybrid expert system may be the SCI distribution for 'hot-spot' regions for the various sized rubber patches by using an adapted SCI chromosome set 1524, which is derived form the steps 1534, 1536 and 1538. Moreover, the neuro-fuzzy inference system as shown in FIG. 15A may be applied again to the intersection points and their SCI values 1518 for the artificial damage, and adapted SCI chromosomes $s_{adapt}^j$ 1524 may be obtained by the use of steps 1418-1426 from output $y_{adapt}^k$ of the neuro-fuzzy inference system shown in FIG. 15A. In step 1534, the difference between the two chromosome set may be calculated to give a root mean square norm E: $E = \sqrt{(s_{prior}^j - s_{adapt}^j)^2}$, j=1, . . . , n×m where n×m is the dimension of the grid points. The fitness value of each chromosome is determined in step 1536 according to the calculated difference: fitness=exp(−E). Then, the genetic operation in step 1538 may be performed for the crossover and mutation of chromosomes, where the operation scheme in this module may use genetic algorithms in the art. Then, the classification module may provide the SCI chromosome distribution 1524 on the grid points, best fitted to the artificial damage. With these SCI chromosomes, an unsupervised neural network can be trained in step 1526 to achieve the clustering or classification on the SCI distribution set on the grid points. However, the classification module can repeat to adapt the hybrid expert system while the process module process to renew the SCI distributions for each excitation frequency.

Figure 16A:
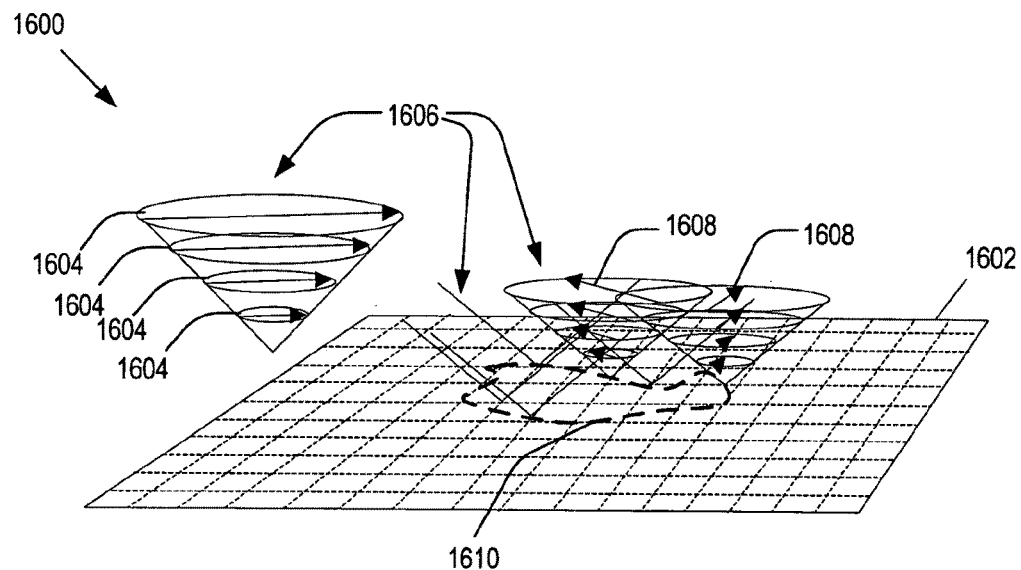
FIG. 16A is a schematic diagram illustrating Gabor jets applied to a 'hot-spot' region in accordance with one embodiment of the present invention.

The classification module may continue to classify the damage types (or, equivalently, 'hot-spot' regions) from the SCI distribution 1540 on the grid points. FIG. 16A is a schematic diagram 1600 illustrating Gabor jets applied to a 'hot-spot' region in accordance with one embodiment of the present invention. As illustrated in FIG. 16, a 'hot-spot' region 1610 may be recognized and segmented from the background SCI distribution 1602 on the grid points. In general, the shape and location of the hot-spot region 1610 may vary according to the excitation frequency and the number of network paths. Also, the diversity in physical characteristic and geometry of structures monitored may increase the difficulty level in classifying the damages. In one embodiment of the present invention, the classification module may employ a multilayer perception (MLP) or feedforward neural network to classify the damage of 'hot-spot' region 1610 in a structure. The classification module may use Gabor wavelet features 1606 to combine those features into a MLP as will be explained later. The Gabor wavelet features 1606 may be obtained from the Gabor wavelet transformation of the SCI distribution with different orientations 1608 and multiresolution scales 1604. The Gabor wavelet function may be defined as $G(x,y) = \exp\{-\pi[(x-x_0)^2\alpha^2 + (y-y_0)^2\beta^2] + 2\pi j[u_0(x-x_0) + v_0(y-y_0)]\}$, where $j=\sqrt{-1}$, $(x_0, y_0)$ are position parameters to localize the wavelet to a selected region, $(u_0, v_0)$ are modulation parameters to orient the wavelet in a preferred direction, and $(\alpha, \beta)$ are scaled parameters. With a set of coefficient called 'Gabor jet', the classification module may compute the Gabor project for multiple orientations and resolutions at a given 'hot-spot' region 1610. Each Gabor jet may contain a number of coefficients corresponding to the number of orientations and the resolution levels such that it consists of logons of orientations and different scales. The classification module can capture local SCI-distribution structure of each of the 'hot-spot' regions by computing a set of Gabor jets at several points of the region to get the input feature.

Figure 16B:
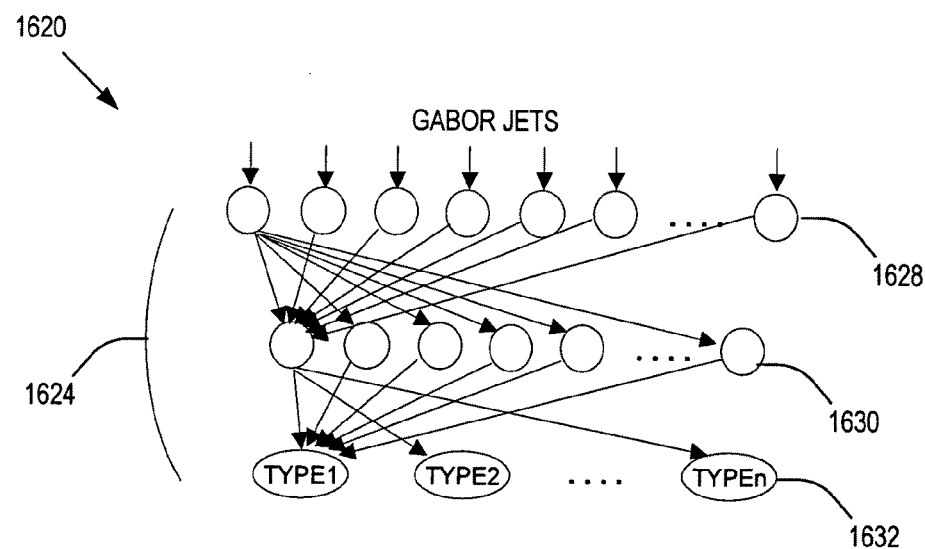
FIG. 16B is a schematic diagram illustrating multilayer perception (MLP) for classifying the types of damages in accordance with one embodiment of the present invention.

FIG. 16B is a schematic diagram 1620 illustrating multilayer perception (MLP) for classifying the type of damage in accordance with one embodiment of the present invention. As illustrated in FIG. 16B, the MLP 1624 may include three layers: an input feature layer 1628 for receiving Gabor jets; a hidden layer 1630; and a output classification layer 1632 for determining the types of damages in hot-spots 1610. A number of neurons in the output classification layer 1632 can be the nodes representing the structural condition types.

FIG. 16C is a schematic diagram 1640 illustrating the fully connected network classifier for classifying a structural condition in accordance with one embodiment of the present invention. As illustrated in FIG. 16C, a set of Gabor jets 1642 may be generated using a SCI distribution 1643 that may contain 3 hot-spot regions 1641. A MLP 1644 may be similar to the MPL 1624 and classify the types of damages in hot-spot regions 1641 into one of the categories C0-C5 1646. For simplicity, only three hot-spots regions 1641 and six categories are shown in FIG. 16C. However, it should be apparent to those of ordinary skill that the present invention may be practiced with any number of hot-spot regions and categories.

FIG. 16D is a schematic diagram 1650 illustrating modular network classifiers for classifying structural conditions in accordance with one embodiment of the present invention. As illustrated in FIG. 16D, a set of Gabor jets 1652 for each hot-spot region 1641 of the SCI distribution 1643 may be generated. Each MLP 1654 may be similar to the MPL 1624 and classify the type of damage in each hot-spot region 1641. Then, a nonlinear transformation and mixing process 1656 may be applied to the results from the MLP 1654 prior to the classification of the damages. The structural condition may be trained with the different condition or damage of structures so that the highest value in the output nodes may be taken to be one of the structural condition types.

For each type of the structural condition or damage, the diagnosis classification module may setup reference templates as a "codebook" in accordance with one embodiment of the present invention. The codebook for each type of damage may be the data set of cluster points of the different versions of SCI distribution or of wavelet transformation coefficients of the SCI distribution, explained later in FIG. 17B. Each template or SCI distribution for the 'hot-spot' region may be clustered by a K-mean and learning vector quantization (LVQ) clustering algorithm. The K-mean algorithm may partition a collection of n vector into c groups $G_i$, i=1, . . . , c and finds a cluster center in each group such that a cost function of dissimilarity measure may be minimized. This algorithm may use an unsupervised learning data clustering method to locate several clusters without using the class information. Once the K-mean algorithm determines the clusters of SCI distribution of the 'hot-spot' region on the grid points, the clustered data may be labeled before moving to the second step of a supervised learning to locate several cluster centers. During the supervised learning, the cluster centers may be fine-tuned to approximate a desired decision hypersurface. The learning method may be straightforward. First, the cluster center c that is closest to the input vector x must be found. Then, if x and c belong to the same class, c is moved toward x; otherwise c is moved form the input vector x. This LVQ algorithm can classify an input vector by assigning it to the same class as the output unit that has the weight vector closest to the input vector. Thus, the LVQ network may use the class information of SCI values to fine-tune the cluster centers to minimize the number of misclassified cases.

Figure 17A:
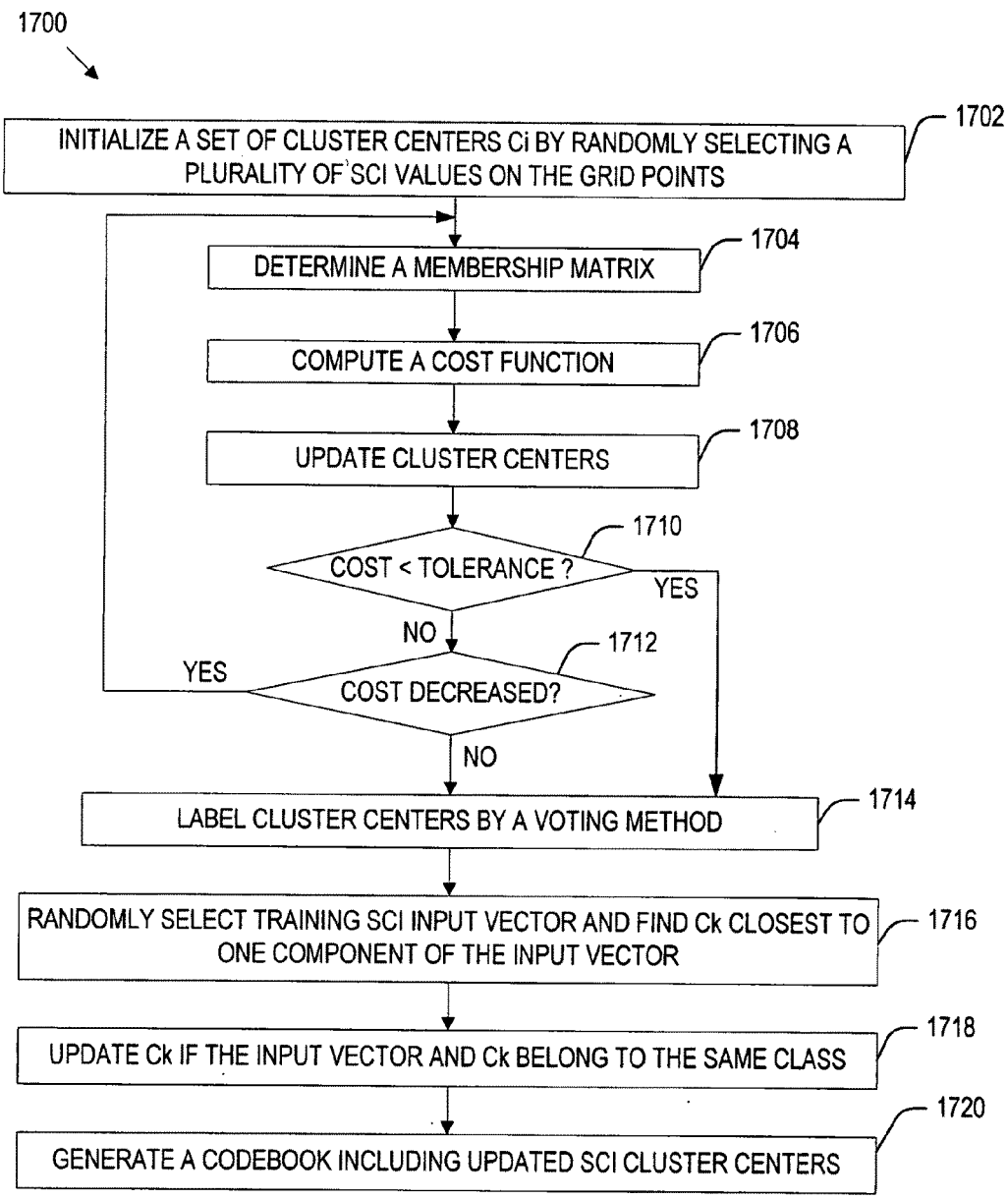
FIG. 17A is a flow chart illustrating exemplary procedures of a K-mean/learning vector quantization (LVQ) algorithm for developing a codebook in accordance with one embodiment of the present invention.

FIG. 17A is a flow chart 1700 illustrating exemplary procedures of a K-mean/LVQ algorithm for developing a clustered 'codebook' in accordance with one embodiment of the present invention. The classification module may begin the first K-mean clustering process, as an unsupervised learning data clustering method, with step 1702 where the cluster centers $c_i$, i=1, . . . , c may be initialized by randomly selecting c points from the SCI data on the 'hot-spot' regions. In step 1704, the classification module may determine the membership matrix S by the equation: $s_{ik}=1$ if $\|x_k-c_i\| \leq \|x_k-c_j\|$; 0 otherwise, where the binary membership matrix S may define the c partition groups of $G_i$, i=1, . . . , c, and x is a randomly selected input vector. Then, the classification module may compute in step 1706 the cost function of $$L = \sum_{i=1}^{c} L_i \text{ and } L_i = \sum_{x_k \in G_i} \|x_k - c_i\|^2$$

where the Euclidean distance may be chosen as the dissimilarity measure between the SCI vector $x_k$ and the corresponding cluster center $c_i$. Next, in step 1708, the cluster centers may be updated according to the equation $$c_i = 1/|G_i| \sum_{x_k \in G_i} x_k$$

and go to decision step 1710 to check if either the cost is below a certain tolerance value. If answer to the step 1710 is YES, the process proceeds to the step 1714. Otherwise, it may proceed to another decision step 1712 to determine if the newly calculated cost is smaller than the previous one. If answer to the step 1712 is NO, the process proceeds to the step 1714. Otherwise, it may proceed to step 1704. Next, the classification module may begin the second LVQ clustering process to fine-tune the cluster centers in step 1714 to minimize the number of misclassified cases. Here, the clusters obtained from the steps 1702-1708 may be labeled by a voting method (i.e., a cluster is labeled class i if it has data points belong to class i as a majority within the cluster.) In step 1716, the classification module may randomly select a training input vector x and find i such that $\|x_k-c_i\|$ is a minimum. Next, in step 1718, the classification module may update $c_i$ by $\Box c_i = \gamma(x_k-c_i)$ if $x_k$ and $c_i$ belong to the same class; otherwise by $\Box c_i = -\gamma(x_k-c_i)$, where $\gamma$ is a learning rate and a positive small constant that may decrease with each of iterations. In step 1720, the classification module can generate a codebook that may include the SCI cluster center of the SCI distribution of the 'hot-spot' regions on the grid points.

Figure 17B:
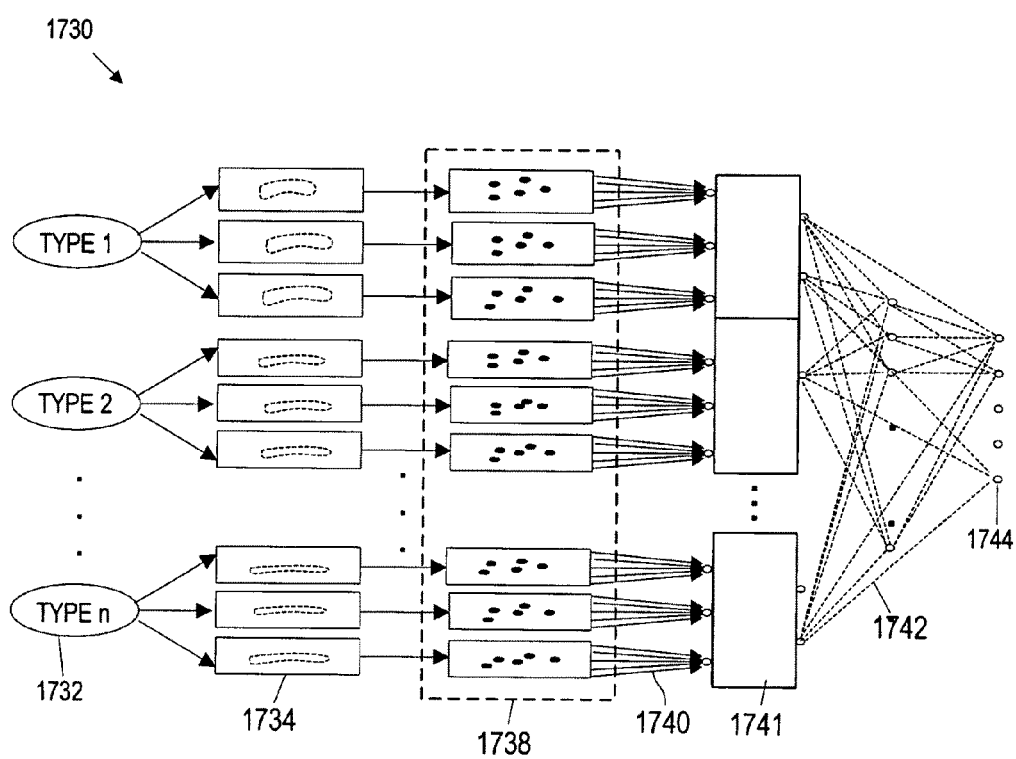
FIG. 17B is a schematic diagram illustrating exemplary procedures of a classification module to build a damage classifier using a codebook generated by the steps in FIG. 17A in accordance with one embodiment of the present invention.

FIG. 17B is a schematic diagram 1730 illustrating exemplary procedures of a classification module to build a damage classifier using a codebook generated by the steps in FIG. 17A in accordance with one embodiment of the present invention. The damages may be located in a 'hot-spot' region on the grid points of the diagnostic network paths. The SCI distribution 1734 of 'hot-spot' regions for each structural condition may be used to design the codevector for structural conditions or damages, where each type of damage may belong to one of the types 1732. Each SCI distribution 1734 may be obtained at an actuation frequency. For the network signals measured at a different excitation frequency, another block template 1738 can be also attained from the collection 1734 on the SCI distributions of the 'hot-spot' regions. The codevector may be given by the set of the cluster centers of the block template of the SCI distribution of the 'hot-spot' regions. Then, the classification codebook 1738 comprising a set of the optimized block templates according to each of the structural condition or damage references may be obtained by differentiating actuation frequency. In order to establish the codebook-based classifiers considering the actuation frequency, a frequency multilayer perception 1740 must be given in the codevectors of the codebook 1738 corresponding to the set of actuation frequencies. The output from the frequency multilayer perception 1740 may be input into a neural network input layer 1741. Then, using the output from the neural network input layer 1741, other multilayer perception 1742 may also classify the structural condition or damage 1744 to combine the outputs of the frequency multilayer perception. In one embodiment of the present invention, the coefficients of Fourier and wavelet transformation of these SCI values instead of the SCI values of the 'hot-spot' regions can be utilized as the input of the K-mean algorithm in FIG. 17A. In another embodiment of the present invention, the principal component analysis, incorporated with Fisher linear discriminant analysis or eigenspace separation transformation, can be used in the PCA-based LVQ clustering method for the SCI distributions or wavelet-transformed SCI distributions to provide different codebooks with high sensitivity to damage types.

Figure 18A:
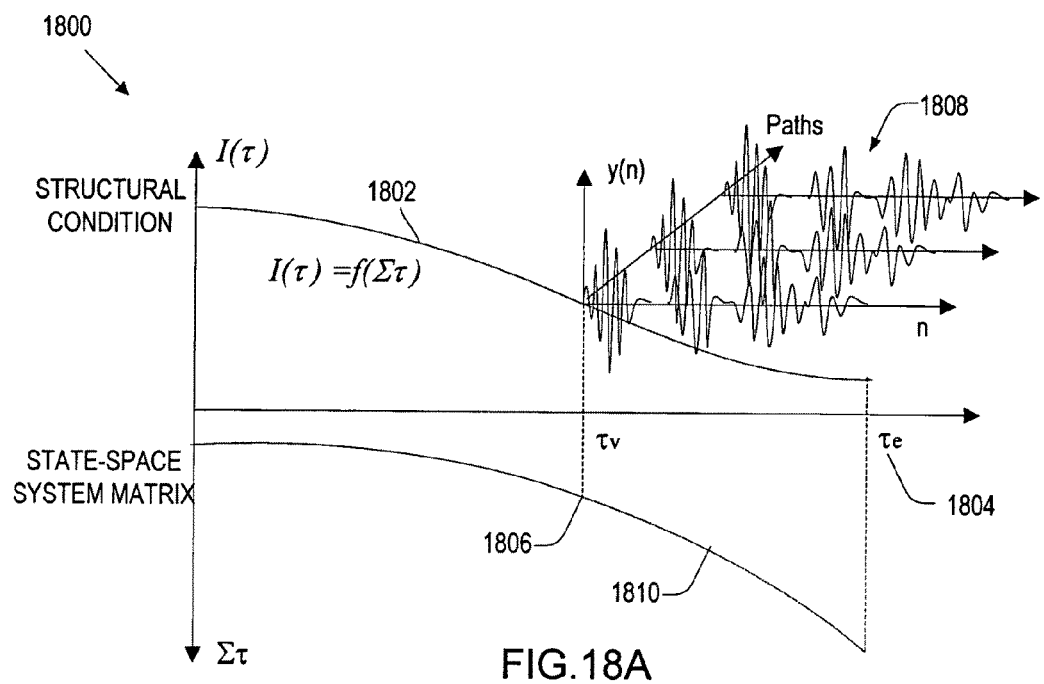
FIG. 18A is a schematic diagram illustrating three evolution domains of a structure in operation/service, dynamics of sensory network system, and network system matrix, according to one embodiment of the present invention.

A structure suffers aging, damage, wear and degradation in terms of its operation/service capabilities and reliability. So, it needs a holistic view that the structural life has different stages starting with the elaboration of need right up to the phase-out. Given a network patch system, the current wave transmission of the network patch system may obey different time scales during the damage evolution to query the structure of its time-variant structural properties. FIG. 18A illustrates a schematic diagram 1800 of three evolution domains of a structure in operation/service, dynamics of the network patch system, and network system matrix in accordance with one embodiment of the present invention. In illustrated in FIG. 18A, a slow-time coordinate $\tau$ designating the structure damage evolution is introduced, and, in addition, the fast-time coordinate n describing the current network dynamics for the wave transmission is introduced.

In the fast timeframe nested in the long-term lifetime, the dynamic system of the diagnostic network patch system, as a black-box model to be identified from the input actuation and output sensing signals, can be described by an autoregressive moving average with exogenous inputs (ARMAX) or state space model. Rather than using the ARMAX model possibly incorporated in a fault diagnostic system to query the functionality of built-in system components, the state-space dynamics models of the network patch system at a fixed lifetime $\tau$ can be used. The state-space dynamic model, considered in non-distributed domain for the brevity of explanation, may be represented by $x_\tau(n+1)=A_\tau x_\tau(n)+B_\tau f(n)$, where the state vector $x_\tau(n)$ is the wave-transmission state vector of the network system and $f(n)$ is the input force vector of the actuators in the network patches. $A_\tau$, $B_\tau$ are the system matrix and the input matrix, respectively. The excitation force for generating Lamb wave in all network paths is assumed to be unchanged during the lifetime of $\tau_e$. The measurement equation of the network sensors is written as $y_\tau(n)=C_\tau x_\tau(n)$ where $y_\tau(n)$ is the sensor signal vector and $C_\tau$ is the system observation matrix. The system matrix $\Sigma_\tau(=[A_\tau,B_\tau,C_\tau])$ of the diagnostic network patch system can be considered independent of the fast time coordinate.

To model the network dynamics of the diagnostic patch system, the prognosis module may compute the system matrix $\Sigma_\tau(=[A_\tau,B_\tau,C_\tau])$ by using a subspace system identification method that reconstructs the dynamic system from the measured actuator/sensor signals in the network patches. The procedures disclosed by Kim et al., "Estimation of normal mode and other system parameters of composite laminated plates," Composite Structures, 2001 and by Kim et al., "Structural dynamic system reconstruction method for vibrating structures, Transaction of DSMC, ASME, 2003, which are incorporated herein in its entirety by reference thereto, can be employed to establish the reconstructed dynamic system model using the multiple inputs and outputs of the present sensory network system.

A fundamental quantity for monitoring and diagnosis may be a symptom contained in sensor signals measured from a time-variant system. The structural condition change or damage of a structure may essentially indicate the modification in wave transmission or dynamic characteristics of the structure system containing the network of a plurality of sensors and actuators a structure. The system matrix $\Sigma_\tau$ is observable and sensitive with respect to the structural condition change so that it can be considered as a symptom. The system matrix as a symptom can be applied one of suitable damage-related dynamic characteristics properties, for example, which may be natural frequencies, damping ratios and vibrational mode shapes to represent structural condition change as sensitive quantities for damage/impact/aging of a structure. Thus, the structural condition index $I(\tau)$ on the diagnostic network paths can be described by a nonlinear function with the variable of the system matrix $\Sigma_\tau$ in the lifetime: $I(\tau)=f(\Sigma_\tau)$. Examples of similar approach can be found in "Damage identification using reconstructed residual frequency response functions", Journal of Sound and Vibration, 2003, by Kim and "Bending rigidity and natural frequency of debonded honeycomb sandwich beams", Composite Structures, 2002, by Kim et al. and "Natural frequency reduction model for matrix-dominated fatigue damage in composite laminates", Composite Structures, 2003, by Moon et al., which are incorporated herein, in its entirety, by reference thereto.

To determine the near future structural condition in damage evolution domain, the prognosis module may employ the current trend of the system matrix as the damage/impact related temporal symptom of a host structure. If the temporal symptom shows sign of deterioration, as exemplified by the change of damage/impact related symptom increasing with time $\tau$, the prognostic module will predict the behavior of the 'hot-spot' regions with respect to the remaining life span of a structure and trigger an early warning. Consequently, the future trend of the system matrix $\Sigma_\tau$ produced by the network dynamics of Lamb-wave transmission on the structure makes it possible to forecast the structure damage/impact conditions. To estimate the future system matrix $\Sigma_\tau$, the prognosis module preferably utilizes a training method of recurrent neural network (RNN) with the previous dynamic reconstruction models determined from the simulated sensor signals, because of its highly nonlinear characteristics of the SCI vector $I(\tau)$. In an alternative embodiment, the feed-forward neural network (FFN) can be used. The curves 1802 and 1810 may represent the evolution of the SCI vector $I(\tau)$ and the matrix $\Sigma_\tau$, respectively, and span up to the time of structural death $\tau_e$ 1804. Sensor signals 1808 may be measured to access the structural conditions at time $\tau_v$ 1806.

Figure 18B:
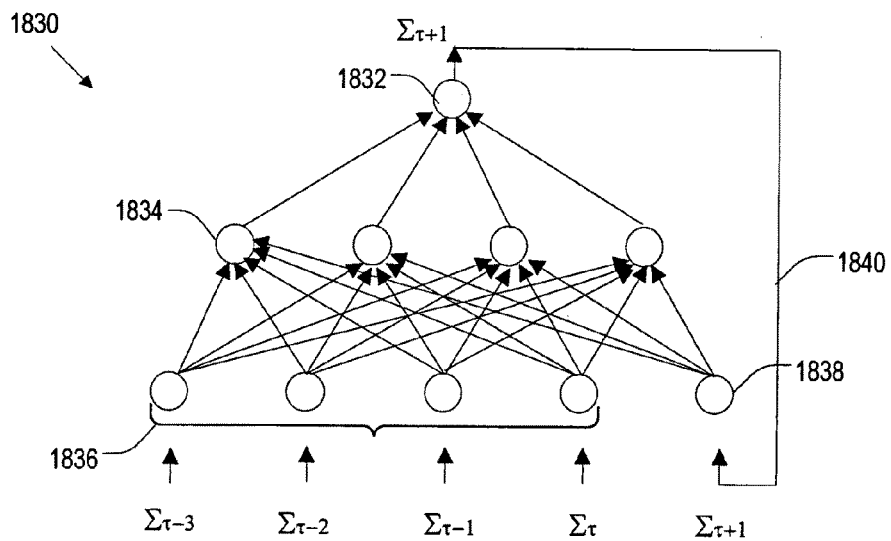
FIG. 18B schematically represents the architecture of a recurrent neural network for forecasting the future system matrix in accordance with one embodiment of the present invention.

FIG. 18B schematically illustrates the architecture of a recurrent neural network 1830 for forecasting the future system matrix in accordance with one embodiment of the present invention. As shown in FIG. 18B, the architecture of the RNN 1830 may have four input nodes 1836 and additional feedback-path node 1838, four hidden nodes 1834 and one output node 1832. The input data set may be a set of the elements of discrete time-delayed system matrix series. The output layer may consist of one neuron 1832 corresponding to the system matrix elements that are being predicted at the first time step in the future. In the RNN 1830, the current activation state of the output is a function of the previous activation states as well as the current inputs. At time $\tau$, the output node (output signal at $\Sigma+1$) may be calculated by the activation of hidden nodes 1834 at the previous time steps $\tau, \tau-1, \tau-2, \ldots, \tau-n$ etc. Therefore, each training pattern will contain the current $\Sigma_\tau$, the previous three time lagged values $\{\Sigma_{\tau-3}, \Sigma_{\tau-2}, \Sigma_{\tau-1}\}$, and an extra input from additional feedback loop 1840, and the output $\hat{\Sigma}_{\tau+1}$ is one step ahead predicted value. This network can provide the estimated value of the next future system matrix based on the current and previous system matrix values. A sigmoid function of $1/(1+e^{-x})$ may be used as the activation functions of the nodes contained in the hidden and output layers. The nodes should operate in the ranges of the activation functions, and all the element data in the system matrix in activation may be scaled to the interval $[-0.5\ 0.5]$. The level of the RNN's learning may be determined by a prediction error between the actual outputs from the network and the target outputs corresponding to an input data set. The error may be utilized in adjusting the weights until the actual outputs are consistent with the target values. The RNN in prognosis module may complete the learning process when the number of training iterations has reached a prescribed number and the error can be judged acceptably small.

By the use of the state-space model of the future system matrix $\hat{\Sigma}_{\tau+1}$, the prognosis module may develop the prognostic sensor signals for the 'hot-spot' regions of the structure from the inputs of the same actuator signals. Now, the identification and classification methods, as explained in FIGS. 9-18B, can apply to the prognostic sensor signals to compute the one-step ahead SCI vector $I(\tau+1)$. Finally, the prognosis module can display the prognostic tomography image and store it into a prognosis tomography database depository.

As mentioned, the monitoring software may comprise interrogation, processing, classification and prognosis modules. These application modules may use eXtensible Markup Language (XML) to save their processed data and/or images to a structured-query-language (SQL) based database and retrieve the reference and system data for device locations, network paths and parameters of structural condition monitoring system. Each XML-formatted document may be described by its data and tags created by the structural monitoring system. Also, each module can parse the XML document to read data that may be input to other application modules. Tags in XML documents may consist of root element in the outmost node and child elements in the nested nodes and may have attributes that appear as name/value pairs following the name of the tag.

The structural health monitoring software can also have Simple Object Access Protocol (SOAP) or RPC (Remote Procedure Call)-XML, which are lightweight protocol for exchanging SCI data and images in a distributed structure computing system for structural condition monitoring. In the distributed server system, all application modules can also be XML web services capable of communicating and remotely computing across network using the open standard SOAP or XML-RPC with XML-formatted documents of structural condition information for all marshaled structure systems. To provide the XML web services for structural health monitoring, the application modules are abstracted as an entity by compiling them with Common Object Module (COM), and then wrapped by applying a SOAP wrapper, such as SOAP Toolkit™ software from Microsoft. The application modules can use a low-level Application Programming Interface (API) for direct control over the SOAP process for their COM objects.

While the present invention has been described with reference to the specific embodiments thereof, it should be understood that the foregoing relates to preferred embodiments of the invention and that modifications may be made without departing from the spirit and scope of the invention as set forth in the following claims.

What is claimed is:

1. A computer-implemented method of identifying damage in a structure, comprising:
   obtaining one or more damage index values for a network coupled to a structure, the network including a plurality of diagnostic network patches (DNPs) attached to the structure, at least one of the plurality of DNPs being for operating as a transmitter patch for transmitting a signal that propagates through the structure, each said DNP being for operating as at least one of a transmitter patch and a sensor patch for sensing the signal, each of the damage index values being a quantity associated with the signal and to be affected by damage in the structure;
   generating, by use of a computer process, a distribution of damage index value over a surface using the obtained damage index values; and
   identifying the damage by analyzing the distribution.

2. The method of claim 1, wherein the step of identifying the damage includes:
   building a damage classifier, and
   classifying the damage by use of the damage classifier.

3. The method of claim 2, wherein the step of building a damage classifier includes:
   training the damage classifier with at least one input data associated with at least one predetermined damage.

4. The method of claim 3, wherein the input data includes a hot-spot region in a distribution of damage index value.

5. The method of claim 3, wherein the input data is generated by wavelet-transforming a hot-spot region in a distribution of damage index value.

6. The method of claim 5, wherein the input data includes wavelets of the wavelet-transformed hot-spot region.

7. The method of claim 3, wherein the damage classifier includes one or more multilayer perceptions (MLPs), each of the MLPs being operative to classify a damage type of the input data.

8. The method of claim 7, wherein the damage classifier further includes a modular network classifier for performing a nonlinear transformation and mixing of outputs from the MLPs.

9. The method of claim 1, wherein the step of identifying the damage includes:
   building a codebook; and
   classifying the damage by use of the codebook.

10. The method of claim 9, wherein the step of building a codebook includes:
    providing a distribution of damage index value that includes at least one hot-spot region;
    clustering the hot-spot region to determine cluster centers of the hot-spot;
    forming a codevector that includes the cluster centers; and
    storing the codevector into the codebook.

11. The method of claim 10, wherein the step of clustering the hot spot region is performed by use of a K-mean clustering algorithm.

12. The method of claim 10, wherein the step of building a codebook further includes:
    fine-tuning the cluster centers.

13. The method of claim 12, wherein the step of fine-tuning the cluster centers is performed by use of a learning vector quantization (LVQ) algorithm.

14. The method of claim 10, wherein the step of clustering the hot-spot region includes:
    utilizing a principal component analysis.

15. The method of claim 14, wherein the step of utilizing principal component analysis includes:
    incorporating a Fisher linear discriminant analysis or an eigenspace separation transformation.

16. The method of claim 1, wherein the step of identifying the damage includes:
    providing a distribution of damage index value that includes at least one hot-spot region;
    clustering the hot-spot region to determine cluster centers of the hot-spot;
    forming a codevector that includes the cluster centers;
    training a frequency multilayer perception (FMP) using the codevector; and
    causing the trained FMP to classify the damage.

17. The method of claim 1, wherein each said damage index value includes at least one of a time-of-arrival of the signal and a spectrum energy of the signal.

18. A computer readable medium carrying one or more sequences of instructions for identifying damage in a structure, wherein execution of one or more sequences of instructions by one or more processors causes the one or more processors to perform the steps of:

obtaining one or more damage index values for a network coupled to a structure, the network including a plurality of diagnostic network patches (DNPs) attached to the structure, at least one of the plurality of DNPs being for operating as a transmitter patch for transmitting a signal that propagates through the structure, each said DNP being for operating as at least one of a transmitter patch and a sensor patch for sensing the signal, each of the damage index values being a quantity associated with the signal and to be affected by damage in the structure;

generating, by use of a computer process, a distribution of damage index value over a surface using the obtained damage index values; and identifying the damage by analyzing the distribution.

19. The computer readable medium of claim 18, wherein the step of identifying the damage includes:

building a damage classifier; and classifying the damage by use of the damage classifier.

20. The computer readable medium of claim 19, wherein the step of building a damage classifier includes:

training the damage classifier with at least one input data associated with at least one predetermined damage.

21. The computer readable medium of claim 18, wherein the step of identifying the damage includes:

building a codebook; and classifying the damage by use of the codebook.

22. The computer readable medium of claim 21, wherein the step of building a codebook includes:

providing a distribution of damage index value that includes at least one hot-spot region;

clustering the hot-spot region to determine cluster centers of the hot-spot;

forming a codevector that includes the duster centers; and storing the codevector into the codebook.

23. The computer readable medium of claim 18, wherein the step of identifying the damage includes:

providing a distribution of damage Index value that includes at least one hot-spot region;

clustering the hot-spot region to determine cluster centers of the hot-spot;

forming a codevector that includes the cluster centers;

training a frequency multilayer perception (FMP) using the codevector; and causing the trained FMP to classify the damage.

24. The computer readable medium of claim 18, wherein the one or more sequences of instructions implement a wireless communication method of Wireless Application Protocol (WAP) or Wireless Markup Language (WML) for the Internet Web Access of a WAP-enabled cell phone, a Pocket PC with a HTML browser, or an HTML-enabled device.

25. A system for identifying damage in a structure, comprising:

means for obtaining one or more damage index values for a network coupled to the structure, the network including a plurality of diagnostic network patches (DNPs) attached to the structure, at least one of the plurality of DNPs being for operating as a transmitter patch for transmitting a signal that propagates through the structure, each said DNP being for operating as at least one of a transmitter patch and a sensor patch for sensing the signal, each of the damage index values being a quantity associated with the signal and to be affected by damage in the structure;

means for generating, by use of a computer process, a distribution of damage index value over a surface using the obtained damage index values; and means for identifying the damage by analyzing the distribution.

26. The system of claim 25, wherein the means for identifying the damage includes:

means for building a damage classifier; and means for classifying the damage by use of the damage classifier.

27. The system of claim 26, wherein the means for building a damage classifier includes:

means for training the damage classifier with at least one input data associated with at least one predetermined damage.

28. The system of claim 25, wherein the means for identifying the damage includes:

means for building a codebook; and means for classifying the damage by use of the codebook.

29. The system of claim 28, wherein the means for building a codebook includes:

means for providing a distribution of damage index value that includes at least one hot-spot region;

means for clustering the hot-spot region to determine cluster centers of the hot-spot;

means for forming a codevector that includes the cluster centers; and means for storing the codevector into the codebook.

30. The system of claim 25, wherein the means for identifying the damage includes:

means for providing a distribution of damage index value that includes at least one hot-spot region;

means for clustering the hot-spot region to determine cluster centers of the hot-spot;

means for forming a codevector that includes the cluster centers;

means for training a frequency multilayer perception (FMP) using the codevector; and means for causing the trained FMP to classify the damage.

* * * * *